United States Patent [19]

Kondo et al.

[11] 4,214,097
[45] Jul. 22, 1980

[54] PROCESS FOR PREPARING DIHALOVINYLCYCLOPROPANECARBOXYLATES

[75] Inventors: Kiyoshi Kondo; Kiyohide Matsui; Akira Negishi, all of Kanagawa; Yuriko Takahatake, Tokyo, all of Japan

[73] Assignee: Sagami Chemical Research Center, Tokyo, Japan

[21] Appl. No.: 870,974

[22] Filed: Jan. 20, 1978

Related U.S. Application Data

[62] Division of Ser. No. 606,807, Aug. 22, 1975.

[30] Foreign Application Priority Data

Feb. 24, 1975 [JP] Japan .................................. 50/21857

[51] Int. Cl.$^2$ ............................................. C07C 69/65
[52] U.S. Cl. ...................................... 560/213; 560/219
[58] Field of Search ............... 560/205, 211, 213, 219; 260/205, 211, 213, 219, 405.5; 562/604

[56] References Cited

U.S. PATENT DOCUMENTS

| 2,561,516 | 7/1961 | Ladd et al. | 560/111 |
| 3,354,196 | 11/1967 | Julia | 260/465 |
| 3,862,978 | 1/1975 | Decker et al. | 560/192 |
| 3,994,953 | 11/1976 | Babler | 560/219 |
| 4,024,163 | 5/1977 | Elliott et al. | 560/124 |

OTHER PUBLICATIONS

Elliott, *Nature*, 244, 456 (1973).
Shelton, Reid J. et al., *J. Org. Chem.*, 23, 1876 (1958).
*Chem. Abstracts*, 8th Coll. Index, p. 22,632S (1971).

*Primary Examiner*—Norman Morgenstern
*Assistant Examiner*—L. Hendriksen
*Attorney, Agent, or Firm*—Robert M. Kennedy; Robert L. Andersen; H. Robinson Ertelt

[57] ABSTRACT

Novel syntheses of dihalovinylcyclopropanecarboxylates, including potent insecticides, are described. The processes begin with the reaction between an alkenol and an orthoester to produce a γ-unsaturated carboxylate, followed by the catalyzed addition of a carbon tetrahalide to the double bond and dehydrohalogenation to produce a cyclopropane derivative.

1 Claim, No Drawings

PROCESS FOR PREPARING DIHALOVINYLCYCLOPROPANECARBOXYLATES

This is a division of application Ser. No. 606,807 filed Aug. 22, 1975.

BACKGROUND OF THE INVENTION

1. Field of the Invention

This invention relates to a new process for preparing organic compounds containing the cyclopropane ring system, particularly substituted cyclopropanes having utility as pyrethroid insecticides or as intermediates in the preparation of pyrethroid insecticides, and to new compositions of matter useful in the practice of this process.

2. Description of the Prior Art

The class of pyrethroid insecticides includes both natural and synthetic members. The active natural products are extracted from the blossoms of pyrethrum flowers (Chrysanthemum cinerariaefolium) grown mainly in East Africa. The composition of the extracts has been elucidated by continuing the classical work of Staudinger [Helv. Chim. Acta, 7, 390 (1924)]. Harper [J. Chem. Soc., 892 (1946)], LaFarge et al. [J. Am. Chem. Soc., 69, 2932 (1947)], Godin et al. [J. Chem. Soc. (C), 3321 (1966)] as well as Crombie et al. [Chem. & Ind., 1109 (1954)] contributed to proving that the extracts comprise at least six closely related vinylcyclopropanecarboxylates: pyrethrin I, pyrethrin II, cinerin I, cinerin II, jasmolin I and jasmolin II. The most important natural pyrethroid is pyrethrin I.

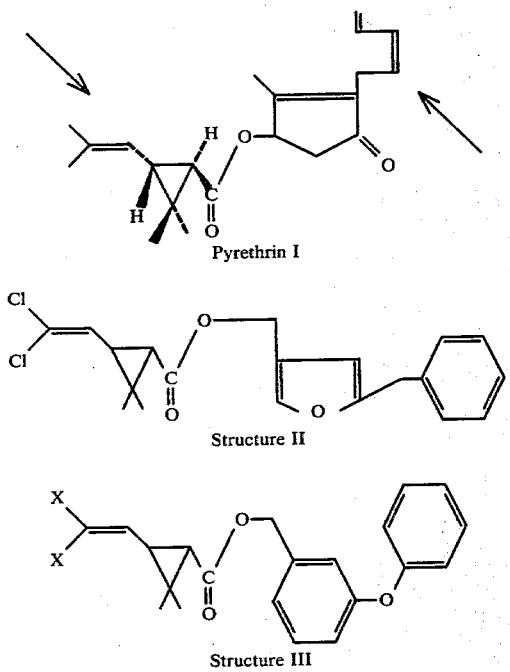

Pyrethrin I

Structure II

Structure III

The structures of the other five components display variations in the portions of the molecule indicated by the arrows. In cinerin II and jasmolin II the dimethylvinyl group at the 2-position becomes (methyl)(carbomethoxy)vinyl; while in the cinerins the pentadienyl side chain in the alcohol moiety is 2-butenyl; in the jasmolins, 2-pentenyl.

In addition to optical isomerism, the pyrethroids display geometrical isomerism in that the hydrogen atoms at the 1 and 2 positions of the cyclopropane ring may be in either a cis or a trans relationship with respect to each other as illustrated in the drawing of the pyrethrin I molecule. The natural pyrethrin extracts comprise the trans forms and it is known that the trans isomers are more active. It is believed that there are two important centers in the pyrethroid structure which especially affect insecticidal activity, namely the substituted vinyl group in the acid moiety and the unsaturated side chain in the alcohol portion of the molecule. The vinyl group is believed to be the site for metabolic attack and detoxification by the insect; whereas the nature of the alcohol moiety is believed to influence the photooxidative stability [Elliott, Chem. & Ind., 978 (1974)].

With the discovery of the structure of the natural pyrethroids and extensions by Campbell et al. [J. Chem. Soc., 283 (1945)] of the work begun by Staudinger, it has been possible to produce synthetic pyrethroids.

Until recently, 1,1,1-trichloro-2,2-(bis-p-chlorophenyl)ethane (DDT) and 1,2,3,4,5,6-hexachlorocyclohexane (BHC) were widely used as insecticides. However, in view of the resistance of these materials to biodegradation and their persistence in the environment, new insecticides producing less environmental harm have been sought. Pyrethroids have long been of interest because they are active against a wide range of insect species, they display relatively low toxicity toward mammals, and they do not leave harmful residues. For example, pyrethrin I is more than 100 times as potent toward mustard beetles (Phaedon cochleariae) as DDT, but only ¼-178 as toxic toward rats [Elliott et al., Chem. & Ind., 978 (1974); Nature, 244, 456 (1973); Chemical Week, April 12, 1969, p. 57].

Although they possess a number of desirable characteristics, the natural pyrethroids undergo rapid biodegradation, they have poor photooxidative stability, their availability is uncertain, and it is costly to extract and process them. For a number of years efforts have been underway around the world to produce synthetic pyrethroid insecticides which would overcome these disadvantages. A notable recent development was the discovery of a dihalovinylcyclopropanecarboxylate (Structure II) having a toxicity toward insects more than 10,000 times greater than that of DDT, with an oral toxicity toward mammals similar to pyrethrin I [Elliott et al., Nature, 244, 456 (1973)]. Although Structure II, in which the alcohol moiety is 5-benzyl-3-furylmethyl, does not have exceptional photooxidative stability, Elliott et al. discovered that 3-phenoxybenzyl analogs (Structure III where X is halogen) were remarkably resistant to photooxidative degradation [Nature, 246, 169 (1973), Belgian Patents 800,006 and 818,811].

The objects of this application are to present processes for the synthesis of pyrethroids in which the cyclopropanecarboxylic acid moiety contains a dihalovinyl group in the 2 position and to describe novel compositions of matter useful in the practice of these processes. Accordingly, processes of this invention lead to esters of such acids which either are or may be converted readily into pyrethroid insecticides. The major advantage of this invention is to provide a convenient synthetic route to pyrethroids of the type represented by Structures II and III.

The early synthetic pyrethroids were compounds in which only the alcohol portion of the ester structure was varied. Synthetic pyrethroids representing this type of variation include allethrin and resmethrin which both contain the dimethylvinyl group of pyrethrin I, but in which the alcohol is allethrolone or 5-benzyl-3-furylmethyl alcohol respectively. Like the natural products, these pyrethroids degrade rapidly in air and light [Elliott et al., Nature, 246, 169 (1973)]. Processes for preparing such pyrethroids generally have begun with chrysanthemic acid, obtained either by the hydrolysis of natural pyrethroids or by the method of Staudinger [Helv. Chim. Acta, 7, 390 (1924)].

Only in recent years has the cyclopropanecarboxylic acid moiety, especially the vinyl group thereof, been modified synthetically. Prior to the present invention, the known methods for varying the nature of the substituents occupying the 2 position in the cyclopropane ring included the following:

(1) Chrysanthemic acid or a naturally occurring chrysanthemate may be subjected to ozonolysis to produce caronaldehyde [Farkas et al., Coll. Czech. Chem. Com., 24, 2230 (1959)]. The aldehyde may then be treated with a phosphonium or sulphonium ylide in the presence of a strong base, followed by hydrolysis [Crombie et al., J. Chem. Soc. (C), 1076 (1970); Brit. Patent 1,285,350]. Such a reaction sequence is shown below.

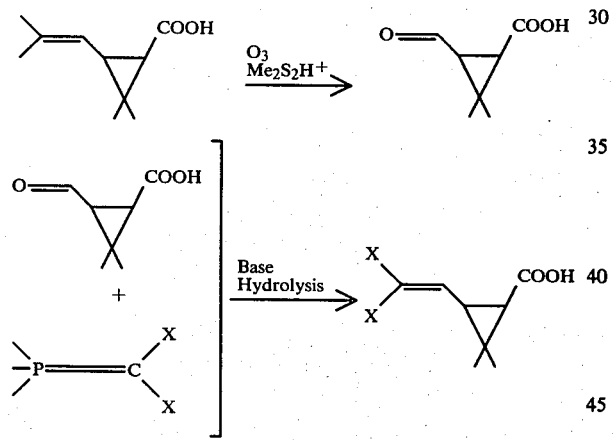

The reaction may be utilized where X is an alkyl group and also where X is halogen [South African Patent 733,528; J. Am. Chem. Soc., 84, 854, 1312, 1745 (1962)]. The reaction has been employed to prepare ethyl 2-(β,β-dichlorovinyl)3,3-dimethylcyclopropane-1-carboxylate, a precursor of Structures II and III. Whereas the ylide reaction proceeds in about 80% yield, the yield of aldehyde from the oxidation is typically only about 20%. The oxidative degradation originated as a tool for proof of structure and was never intended for large-scale preparative use. The oxidation alone requires many hours to complete because mild conditions must be used to minimize the possibility of a violent oxidation of the organic compound. An overall yield of 16% may not be unacceptable when the process is used in research, but it is much too low to be of practical commercial utility. In addition, the starting material is costly since, in essence, it is akin to the compound which is being prepared.

(2) The original Staudinger synthesis of chrysanthemic acid involved the reaction of ethyl diazoacetate with 2,5-dimethylhexa-2,4-diene followed by saponification of the ester [Helv. Chim. Acta, 7, 390 (1924)]. Carbene addition to an unsaturated carbon-carbon linkage has become a general reaction for the preparation of the cyclopropane ring system [Mills et al., J. Chem. Soc., 133 (1973), U.S. Pat. Nos. 2,727,900 and 3,808,260]. Such a reaction, illustrated below, has been employed in the preparation of pyrethroids and also ethyl 2-(β,β-dichlorovinyl)-3,3-dimethylcyclopropane-1-carboxylate, precursor of II and III [Farkas et al., Coll. Czech. Chem. Comm., 24, 2230 (1959)]. In preparing the latter, the starting material may be the mixture of pentenols obtained by the condensation of chloral with isobutylene.

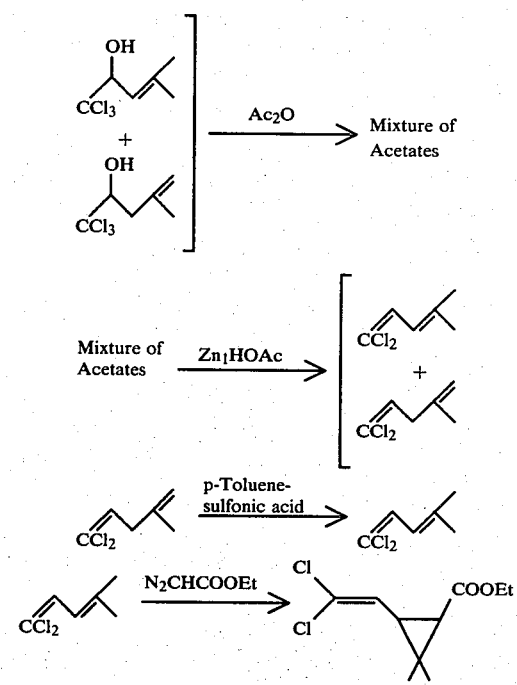

The conversion of the mixture of pentenols to 1,1-dichloro-4-methyl-1,3-pentadiene, short of the cyclopropanecarboxylate, is reportedly only about 50%. This, coupled with the fact that in the last step the production of the diazo ester and its handling are extremely dangerous on a large scale, seriously limits the utility of the process. Furthermore, it is estimated that, should a pyrethroid of Structure III become a major agricultural commodity, commercial production by this method of enough of the dihalovinylcyclopropanecarboxylate to satisfy the potential demand might exhaust the world supply of zinc.

(3) Julia has described a third general method capable of allowing the substituents in the 2 position of the cyclopropane ring to be varied [U.S. Pat. Nos. 3,077,496, 3,354,196 and 3,652,652; Bull. Soc. Chim. Fr., 1476, 1487 (1964)]. According to this method, illustrated below, an appropriately substituted lactone is first treated with a halogenating agent, opening the ring, followed by base-induced dehydrohalogenation, forming a cyclopropane. Even in the relatively uncomplicated case where the terminal

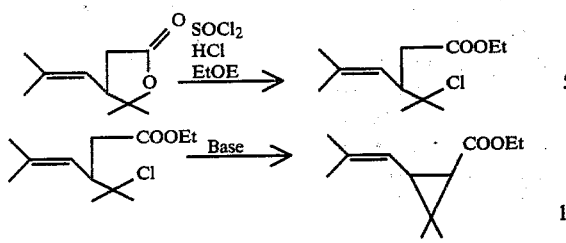

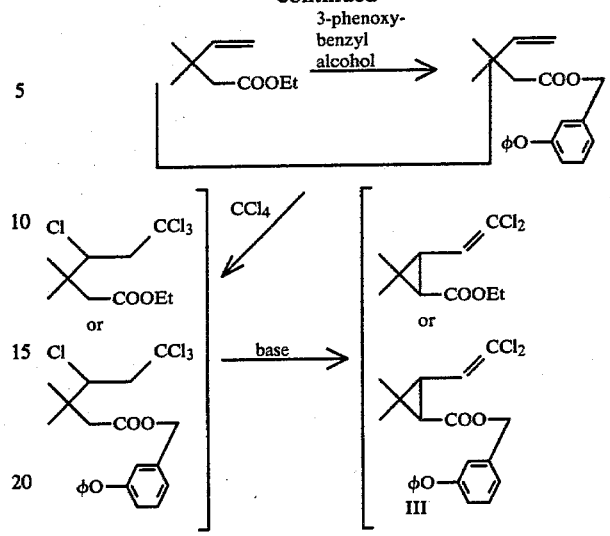

substituents on the vinyl group are methyl and the product is ethyl chrysanthemate, the yield is only 40%. Moreover, lactones of special interest, such as 3-($\beta,\beta$-dichlorovinyl)-4-methyl-$\gamma$-valerolactone are not readily available. Even 3-isobutenyl-4-methyl-$\gamma$-valerolactone, from which ethyl chrysanthemate is made, requires a 3-step synthesis from 2-methylhex-2-en-5-one, including a Grignard reaction. Grignard reactions are difficult to carry out on a large scale and, in any case, could probably not be utilized without destroying a dihalovinyl group were it present.

Thus, the processes taught in the prior art for varying the nature of the substituents occupying the 2 position in the cyclopropane ring, particularly processes for introducing a 2-dihalovinyl group, suffer from a number of disadvantages, the most serious of which are:

(1) The yields of cyclopropanecarboxylates are too low for practical application in commerce;

(2) The starting materials are not readily available, requiring additional synthetic steps, adding to costs and increasing the price of the product beyond that which the market will bear;

(3) The processes all involve at least one reaction which is difficult and dangerous to carry out on a large scale, inviting the risk of fire or explosion.

SUMMARY OF THE INVENTION

It has now been found that the serious disadvantages inherent in the processes of the prior art can be largely overcome by novel syntheses, which proceed in high yield, using readily available, comparatively inexpensive starting materials, in a few safe, commercially feasible steps, via novel compositions of matter as intermediates, to produce pyrethroids of the type represented by Structures II and III or intermediates converted readily into such pyrethroids. The synthetic steps employed in the processes of this invention proceed in high yield: yields of 90% or higher are common. In addition, dihalovinylcyclopropanecarboxylates in which the more active trans isomer ranges in amount from 50% to 90% can be made with almost no variation in yield.

The novel processes of this invention are illustrated specifically by the following chemical equations and Examples wherein, starting with readily available 3-methyl-2-buten-1-ol and ethyl orthoacetate, either the potent, persistent pyrethroid, III, or ethyl 2-($\beta,\beta$-dichlorovinyl)-3,3-dimethylcyclopropanecarboxylate, an intermediate in the preparation of III, is produced.

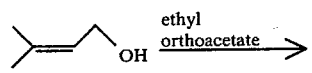

In the Examples which follow, temperatures are in degrees centigrade. Where ir spectra are given, only the frequencies of the most prominent absorption maxima appear. Tetramethylsilane was employed as an internal standard for the nmr spectra. In reporting the nmr data the abbreviations have the following significance: s, singlet; d, doublet; t, triplet; q, quartet; m, multiplet. Any of these abbreviations may be preceded by b for broad or d for double, for example, d.d., double doublet; b.t., broad triplet.

EXAMPLE I

Synthesis of 3-Phenoxybenzyl 2-($\beta,\beta$-Dichlorovinyl)-3,3-dimethylcyclopropanecarboxylate A. Preparation of ethyl 3,3-dimethyl-4-pentenoate A mixture of 0.65 g of 3-methyl-2-buten-1-ol, 2.43 g of ethyl orthoacetate and 50 mg of phenol was heated at 120° with stirring. After 2 hours, the temperature was increased to 140° where it was maintenance for 20 hours. When ethanol evolution had ceased, the mixture was dissolved in benzene to a total volume of 5 ml. Gas chromatographic analysis of the benzene solution showed that ethyl 3,3-dimethyl-4-pentenoate had been produced in 92% yield (see Example V for physical properties).

B. Transesterification between 3-phenoxybenzyl alcohol and ethyl 3,3-dimethyl-4-pentenoate A mixture of 374 mg of ethyl 3,3-dimethyl-4-pentenoate, 400 mg of 3-phenoxybenzyl alcohol and 16 mg of sodium ethoxide in 10 ml of toluene was heated under reflux for 24 hours, with a Dean-Stark apparatus containing a molecular sieve to absorb the evolved ethanol. The mixture was neutralized by adding an anhydrous ether solution of hydrogen chloride. The neutral solution was poured into water. The ether layer was separated, dried over magnesium sulfate, and distilled to give 520 mg (70% yield) of 3-phenoxybenzyl 3,3-dimethyl-4-pentenoate, b.p. 155–158°/0.3 mm.

Analysis: Calculated for $C_{20}H_{22}O_3$: C, 77.39; H, 7.14. Found: C, 77.14; H, 7.11.

nmr δ ppm (CCl$_4$): 7.32–7.08 (m, 4H), 7.05–6.70 (m, 5H), 5.76 (d.d., 1H), 4.92 (s, 2H), 4.96–4.70 (m, 2H), 2.22 (s, 2H), 1.08 (s, 6H).

C. Addition of carbon tetrachloride to 3-phenoxybenzyl 3,3-dimethyl-4-pentenoate A mixture of 245 mg of 3-phenoxybenzyl 3,3-dimethyl-4-pentenoate in 5 ml of carbon tetrachloride was charged to a pressure vessel, and to it was added 2 mg of benzoyl peroxide. The vessel was purged with argon and sealed. The sealed vessel was heated for 5 hours at 140°, then cooled, and an additional 2 mg of benzoyl peroxide was added. The vessel again was purged, sealed and heated at 140° for 5 hours. The procedure was repeated twice more after which the vessel was cooled and the contents were washed successively with water, saturated aqueous sodium bicarbonate and water. The washed mixture was dried over magnesium sulfate, and the solvent was removed under reduced pressure. The residue was purified by silica gel chromatography with benzene as the eluting solvent to give 300 mg (82% yield) of 3-phenoxybenzyl 4,6,6,6-tetrachloro-3,3-dimethylhexanoate.

Analysis: Calculated for $C_{21}H_{22}Cl_4O_3$: C, 54.33; H, 4.78; Cl, 30.55. Found: C, 54.76; H, 4.88; Cl, 30.24.

nmr δ ppm (CCl$_4$): 7.35–7.05 (m, 4H), 7.05–6.75 (m, 5H), 4.96 (s, 2H), 4.30 (d.d., 1H), 3.30–2.80 (m, 2H), 2.57 (d, 1H), 2.26 (d, 1H), 1.15 (s, 3H), 1.07 (s, 3H).

D. Simultaneous cyclization and dehydrochlorination

A solution of 200 mg of 3-phenoxybenzyl 4,6,6,6-tetrachloro-3,3-dimethylhexanoate in 1 ml of anhydrous tetrahydrofuran was added dropwise to a suspension of 124 mg of sodium t-butoxide in 5 ml of anhydrous tetrahydrofuran during which the reaction mixture was cooled in ice. After 1 hour, the mixture was allowed to warm to room temperature and then it was heated under reflux for 1 hour. The mixture was neutralized by the addition of an anhydrous ether solution of hydrogen chloride. The neutralized mixture was poured into ice water and extracted with diethyl ether. The ether extract was dried over magnesium sulfate, and the solvent was removed under reduced pressure. The residue was purified by column chromatography, using a silica gel column with benzene as the eluting solvent, to give 126 mg (75% yield) of 3-phenoxybenzyl 2-(β,β-dichlorovinyl)-3,3-dimethylcyclopropanecarboxylate.

Analysis:
nmr δ ppm (CCl$_4$): 6.80–6.50 (m, 9H), 6.25 (b.d, 0.5H), 5.60 (d, 0.5H), 5.05 (s, 2H), 2.40–1.40 (m, 2H), 1.40–1.05 (m, 6H).

EXAMPLE II

Synthesis of Ethyl 2-(β,β-Dichlorovinyl)-3,3-dimethylcyclopropanecarboxylate

A. Addition of carbon tetrachloride to ethyl 3,3-dimethyl-4-pentenoate

To a solution of 135.2 mg (0.5 mmole) of ferric chloride hexahydrate and 146.3 mg (2.0 mmoles) of n-butylamine in 2.19 g of dimethylformamide contained in a pressure vessel was added 1.56 g (10 mmoles) of ethyl 3,3-dimethyl-4-pentenoate and 4.26 g (30 mmoles) of carbon tetrachloride. The vessel was sealed and heated for 15 hours at 100°. The vessel was then cooled, and the contents were dissolved in diethyl ether. The ethereal solution was washed successively with 1N hydrochloric acid, saturated aqueous sodium bicarbonate and saturated aqueous sodium chloride. The washed solution was dried over magnesium sulfate and distilled to give 2.79 g (90% yield) of ethyl 4,6,6,6-tetrachloro-3,3-dimethylhexanoate, b.p. 116°/0.18 mm.

Analysis: Calculated for $C_{10}H_{16}Cl_4O_2$: C, 38.74; H, 5.20; Cl, 45.74. Found: C, 38.91; H, 5.07; Cl, 45.85.

nmr δ ppm (CCl$_4$): 4.37 (d.d., 1H), 4.07 (q. 2H), 3.40–2.85 (m, 2H), 2.40 (q, 2H), 1.27 (t, 3H), 1.2 (t, 3H), 1.20 (d, 6H).

B. Simultaneous cyclization and dehydrochlorination

Into a solution of 3.1 g (10 mmoles) of ethyl 4,6,6,6-tetrachloro-3,3-dimethylhexanoate in 40 ml of absolute ethanol was added dropwise 20 ml of an ethanol solution containing 1.5 g (22 mmoles) of sodium ethoxide. The mixture was stirred at room temperature for 1 hour after the addition was completed, then refluxed for 1 hour. The mixture was reduced by distillation to about one-tenth its original volume and cooled with ice, and the residue was neutralized by the addition of 1N hydrochloric acid. The neutral solution was extracted with diethyl ether, and the ether extract was washed successively with saturated aqueous sodium bicarbonate and saturated aqueous sodium chloride. After drying over magnesium sulfate, the solution was distilled to give 2.12 g (89% yield) of ethyl 2-(β,β-dichlorovinyl)-3,3-dimethylcyclopropanecarboxylate, b.p. 77°/0.3 mm (see Example III for physical properties).

The novel processes just described specifically are capable of general application as represented by the following chemical equations:

Step 1

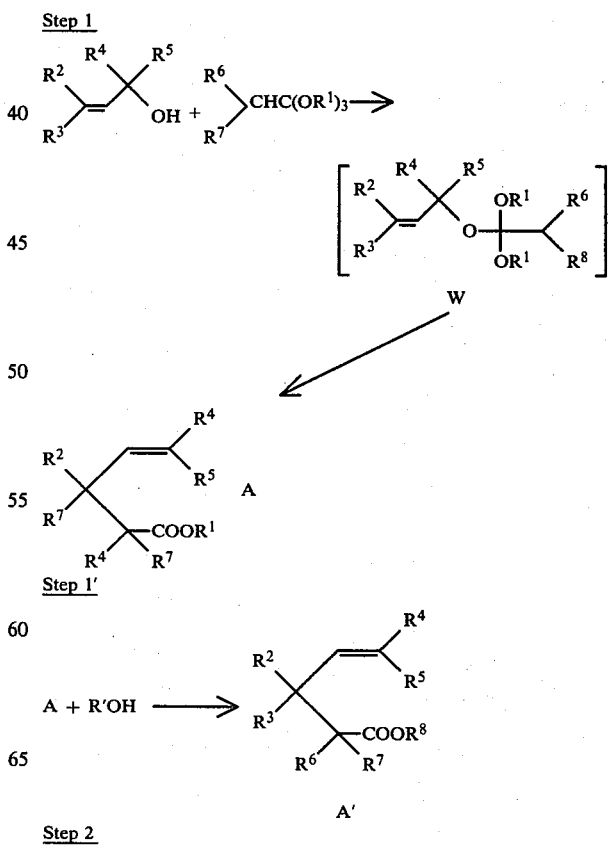

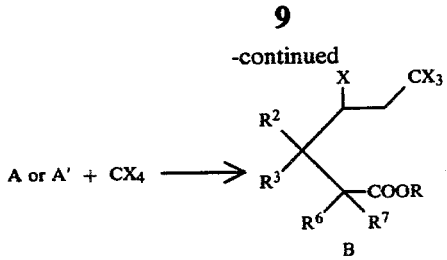

Step 3

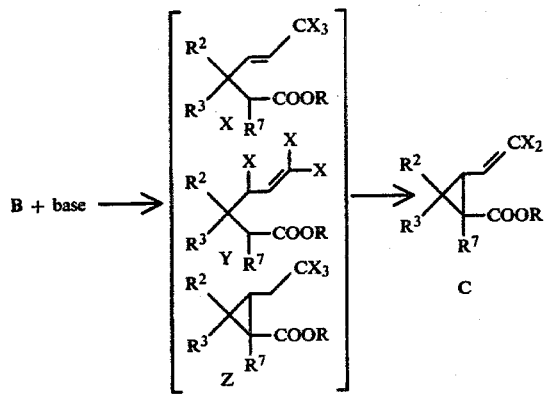

In defining the substituent R groups, the term "lower", modifying such expressions as alkyl, alkene, alkoxy, etc., means 1-6 carbon atoms, preferably 1-4 carbon atoms. X is a halogen atom. The radicals —COOR$^1$ and —COOR$^6$ are carboxylate functions; OR$^1$ and OR$^8$ are alcohol residues in which R$^1$ is a lower alkyl group and R$^8$ is represented by the formula:

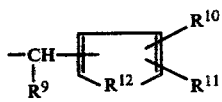

wherein,

R$^9$ is a hydrogen atom or a cyano group;

R$^{10}$ is a hydrogen atom, a lower alkyl group, a phenoxy group, a benzyl group or a phenylthio group;

R$^{11}$ is a hydrogen atom or a lower alkyl group; and

R$^{12}$ is a divalent oxygen or sulfur atom or a vinylene group, —CH=CH—.

R is either R$^1$ or R$^8$.

Except as otherwise specified in the detailed descriptions for each step, the radicals R$^2$–R$^7$ appearing in the equations may be the following:

Each of R$^2$–R$^7$ is a hydrogen atom, a lower alkyl group, a lower alkenyl group, a lower alkynyl group, a lower cycloalkyl group, a phenyl group, an aralkyl group such as benzyl, a lower alkoxycarbonyl group, a lower alkanoyl group, an aroyl group such as benzoyl, a di(lower alkyl)amide group, a nitrile group or a lower haloalkyl group; the couples R$^2$–R$^3$, R$^4$–R$^5$, and R$^6$–R$^7$ may constitute lower alkylene chains of at least 2 carbon atoms.

In the process of Step 1 an alkenol is reacted with an orthoester to produce a γ-unsaturated carboxylate, Structure A. It has been found that the mixed orthoester, Structure W, is an intermediate and may be isolated. Other reactants capable of producing this intermediate, useful in the practice of the process, could be employed to produce A; for example, an alkenol may be reacted with an appropriate ketene acetal to produce such a mixed orthoester from which the γ-unsaturated carboxylate, A, may be derived. The product of Step 1 is a lower alkyl ester which may optionally be reacted in Step 1' by ester interchange with an alcohol, R$^8$OH, chosen from among alcohols which commonly appear in pyrethroids; for example, 3-phenoxybenzyl alcohol. The ester so produced, Structure A', can be carried through the processes of Steps 2 and 3 to yield, as the product of Step 3, a dihalovinylcyclopropanecarboxylate which is a pyrethroid insecticide.

In the process of Step 2, the γ-unsaturated carboxylate, A or A', is then treated with a carbon tetrahalide to produce a γ-halocarboxylate of Structure B. The γ-halocarboxylate may be dehydrohalogenated subsequently with a base to produce any one of four different products, depending upon the choice of reaction conditions. The novel intermediates represented by Structures X, Y and Z, each representing the elimination of 1 mole of HX from the γ-halocarboxylate, B, may, but need not, be isolated. Each of the intermediates, X, Y and Z, is a useful composition of matter which can be carried to the dihalovinylcyclopropanecarboxylate, Structure C, by the elimination of additional HX. If the optional ester interchange of Step 1' was not carried out on the γ-unsaturated carboxylate, A, the dihalovinylcyclopropanecarboxylate, C, may be treated by known processes to produce an active insecticide [Elliott, Nature, 244, 457 (1973)].

Step 1

The first process of this invention is represented by Step 1 in which an alkenol is reacted with an orthoester to produce a γ-unsaturated carboxylate, A, via the mixed orthoester, W, an intermediate which may or may not be isolated. Examples of alkenols which may be employed in the process of Step 1 are allyl alcohol, crotyl alcohol, 4-methyl-1-phenyl-3-penten-2-ol, 4-methyl-3-penten-2-ol, cinnamyl alcohol, 3-methyl-2-buten-1-ol, 2,4-dimethyl-3-penten-2-ol, 5-methyl-4-hexen-3-ol, 2-methyl-2-hepten-4-ol, 1-cyclopentyl-3-methyl-2-buten-1-1-ol and the like. The specific alkenol to be employed in Step 1 will depend upon the desired nature of R$^2$, R$^3$, R$^4$, and R$^5$. These alkenols are readily available or are derived easily from commercial raw materials. In order to produce a 2-dihalovinylcyclopropanecarboxylate such as II or III, having dimethyl substitution in position 3 of the cyclopropane ring, 3-methyl-2-buten-1-ol is preferably employed. 3-Methyl-2-buten-1-ol is available as a by-product from the manufacture of isoprene.

Examples of orthoesters which may be employed in the process of Step 1 include, in the acid part, alkanoic acids such as acetic acid, propionic acid, butyric acid, isobutyric acid and valeric acid; and in the alcohol part, lower alkanols such as methanol and ethanol; e.g., ethyl orthopropionate, methyl orthoacetate, ethyl orthoacetate, etc. The acid and alcohol portions of the orthoester will be chosen to yield the desired R$^1$, R$^6$, and R$^7$ groups in the γ-unsaturated carboxylate. The orthoesters may be prepared readily by the alcoholysis of the corresponding nitriles. In producing a γ-unsaturated carboxylate which is to be carried through the remaining processes of this invention to yield a dihalovinylcyclopropanecarboxylate, ethyl orthoacetate is preferably employed.

Although the reaction between the alkenol and the orthoester does not require it, an acid catalyst increases the rate of the reaction. Examples of acid catalysts which may be employed include phenols such as phenol, ortho, meta or para-nitrophenol, ortho, meta or para-cresol, ortho, meta or para-xylenol, 2,6-dimethylphenol, 2,6-di-t-butyl-phenol, 2,4,6-tri-sec-butylphenol, 2,4,6-tri-t-butylphenol, 4-methyl-2,6-di-t-butylphenol, 4-methyl-3,5-di-t-butylphenol, hydroquinone, 2,5-di-t-butylhydroquinone, α or β-naphthol and the like; lower aliphatic acids such as acetic acid, propionic acid, butyric acid, isobutyric acid, cyclohexanecarboxylic acid, valeric acid and the like; aromatic carboxylic acids such as benzoic acid, meta-chlorobenzoic acid and the like; sulfonic acids such as benzenesulfonic acid, para-toluenesulfonic acid and the like; inorganic acids such as hydrochloric acid, sulfuric acid, phosphoric acid, boric acid and the like; and Lewis acids such as zinc chloride, ferric chloride, mercuric acetate and the like. In order to avoid side reactions such as dehydration of the alkenol, phenols, aliphatic acids having 2 to 6 carbon atoms and aromatic acids are preferred, with phenol being the catalyst of choice in most instances.

The process of Step 1 does not require a solvent, but solvents which do not adversely affect the reaction or the product may be employed if desired. Useful solvents include decalin, n-octane, toluene, ortho, meta or para-xylene, di-n-butyl ether, N,N-dimethylformamide and the like.

Although the stoichiometry suggests that the alkenol and the orthoester should be present in equimolar amounts, it is preferred that a slight excess of the orthoescer be employed. The acid catalyst can be used in an amount ranging from about 0.001 to 20% by weight, preferably from 1 to 15% by weight, based on the amount of alkenol reacted.

The process of Step 1 can be conducted at temperatures ranging from about 20° to 250° C. It is preferred, however, to conduct the reaction in two stages, the first stage at a temperature ranging between 20° and 120° C. and the second stage at a temperature between 100° and 250° C. If ethyl orthoacetate is employed as a reactant, and the reaction is conducted at atmospheric pressure, it is preferable to conduct the first stage at a temperature between about 100° and 120° C., removing ethanol by distillation as it is produced: the second stage is preferably conducted at a temperature between about 140° and 170° C.

Step 1'

The γ-unsaturated carboxylate, A, may, if desired, be reacted according to the process of Step 1' in which the alcohol residue, $OR^8$, is interchanged for the lower alkanol residue, $OR^1$, to produce the γ-unsaturated carboxylate, A', $OR^8$ being chosen from among alcohol residues which commonly appear in pyrethroids. The γ-unsaturated carboxylate, A', when carried through the processes of this invention represented by Steps 2 and 3, may lead directly to a dihalovinylcyclopropanecarboxylate, C, which is a pyrethroid insecticide; e.g., Structure III.

The structure of the γ-unsaturated carboxylate, A, available for the process of Step 1' will depend upon the structures of the starting materials employed in Step 1.

For the purposes of the process of Step 1':

$R^2$ and $R^3$ each is a hydrogen atom, a lower alkyl group, a lower alkenyl group, a lower alkynyl group, a lower cycloalkyl group, a phenyl group or an aralkyl group such as benzyl; $R^2$ and $R^3$ together may constitute a lower alkylene chain of at least 2 carbon atoms; and when one of $R^2$ and $R^3$ is other than hydrogen, the other may be a lower alkoxycarbonyl group, a lower alkanoyl group, an aroyl group such as benzoyl, a di(lower alkyl)amide group or a nitrile group. $R^4$-$R^7$ each is a hydrogen atom, a lower alkyl group, a lower alkenyl group, a lower alkynyl group, a lower cycloalkyl group, a phenyl group or an aralkyl group such as benzyl; the couples $R^4$-$R^5$ and $R^6$-$R^7$ may constitute lower alkylene chains of at least 2 carbon atoms.

The γ-unsaturated carboxylate and the alcohol may be employed in equimolar amounts, but it is preferable that one reactant be in excess. The ethyl ester is convenient to use, and when used, it is preferred that sodium ethoxide be added as a catalyst and that ethanol be removed from the mixture as it is formed. A solvent such as toluene may be employed.

Instead of introducing $R^8$ in the manner just described, the interchange may be conducted at another point in the process, and other synthetic methods can be used for converting an $R^1$ ester to an $R^8$ ester such as hydrolysis followed by esterification, for example, reaction of a dihalovinylcyclopropanecarboxylic acid chloride with an alcohol $R^8OH$ in the presence of a base.

Step 2

The process of this invention represented by Step 2 is a reaction between a γ-unsaturated carboxylate, A or A', and a carbon tetrahalide, $CX_4$, in the presence of a catalyst to produce a γ-halocarboxylate, B. The γ-unsaturated carboxylate, A or A', may be prepared as described above.

For the purposes of the process of Step 2:

$R^2$, $R^3$, $R^4$ and $R^7$ each is a hydrogen atom, a lower alkyl group, a lower cycloalkyl group, a phenyl group, an aralkyl group such as benzyl, a lower alkoxycarbonyl group, a lower alkanoyl group, an aroyl group such as benzoyl, a di(lower alkyl)amide group, a nitrile group or a lower haloalkyl group: the couples $R^2$-$R^3$ and $R^6$-$R^7$ may constitute lower alkylene chains of at least two carbon atoms.

$R^4$ and $R^5$ are hydrogen atoms.

Carbon tetrahalides which may be employed in this process include carbon tetrachloride, carbon tetrabromide, bromotrichloromethane, bromochlorodifluoromethane and iodotrichloromethane. In general, the carbon tetrahalide will contain no more than two fluorine atoms, and no more than one iodine atom. When it is desired to produce a dichlorovinylcyclopropanecarboxylate by the processes of this invention, carbon tetrachloride, bromotrichloromethane or dibromodichloromethane may be employed; although bromotrichloromethane reacts smoothly, carbon tetrachloride is more readily available and less expensive.

The process of Step 2 requires a catalyst, and two distinct types of catalyst systems have been found to be useful; (1) free radical initiators or (2) transition metal salts and coordination complexes between transition metal salts and various electron donors such as organic amines, carbon monoxide, acetylacetone, etc. The reaction can also be catalyzed by radiation; e.g., ultraviolet light, a variant of the reaction employing a free radical catalyst. In order for the reaction to be effectively catalyzed by visible light, the carbon tetrahalide should preferably contain at least one bromine or iodine atom.

Examples of free radical catalysts which may be used include azobisisobutyronitrile (AIBN), benzoyl peroxide (BPO), acetyl peroxide, di-t-butyl peroxide, t-butyl peracetate, t-butyl perbenzoate, t-butyl perphthalate, t-butyl hydroperoxide and the like. The use of a catalytic amount of a free radical catalyst is generally sufficient, but amounts as high as 20% based on the number of moles of γ-unsaturated carboxylate may be employed, especially if the catalyst is added in increments.

Examples of transition metal salts which can be used are cuprous or cupric chloride, ferrous or ferric chloride, cobalt, nickel, zinc, palladium, rhodium or ruthenium chloride, copper cyanide, copper thiocyanide, copper oxide, copper sulfide, copper or iron acetate, iron citrate, iron sulfate, iron oxide, copper or iron acetylacetonate and the like, including hydrates of the salts listed.

Examples of organic amines which can be used in conjunction with the transition metal salts are aliphatic amines such as n-butylamine, diisopropylamine, triethylamine, cyclohexylamine, benzylamine, ethylenediamine, ethanolamine and the like; aromatic amines such as aniline, toluidine and the like; heterocyclic amines such as pyridine and the like; as well as amine salts such as diethylamine hydrochloride and the like. With a view to the availability of materials and optimum yield, a combination of a transition metal halide and an aliphatic amine is preferred, especially ferric chloride hexahydrate and n-butylamine. In order to obtain the maximum yield of the desired product it has been found desirable to employ morethan about 1.5 moles, preferably between about 2 and 10 moles, of organic amine per mole of transition metal salt. In general, the transition metal catalyst may be used in catalytic amounts, about 0.01% based on the number of moles of γ-unsaturated carboxylate, but higher concentrations increase the reaction rate, and 10% or more may be used to advantage.

When a free radical catalyst is employed, it is preferable to use approximately equimolar amounts of the starting materials in the absence of a solvent. However, if desired, solvents which do not adversely affect the reaction; for example, carbon disulfide or hydrocarbon solvents such as benzene or toluene may be used. The reaction may also be conducted in the presence of an excess amount of the carbon tetrahalide as a solvent; the excess can be recovered and recycled. The reaction is preferably conducted at a molar ratio of carbon tetrahalide to γ-unsaturated carboxylate between about 1:1 and 4:1.

When catalyzed by light, the reaction may be conducted at temperatures between about 25° and 100° C. When free radical catalysts are used, the reaction is generally conducted at a temperature between about 50° and 150° C.

When a transition metal salt or a coordination complex is used as the catalyst, the reactants may be in approximately equimolar amounts, but the carbon tetrahalide may also be employed in excess. A solvent is not necessarily required in the reaction, but solvents which do not adversely affect the reaction or the product may be employed if desired; for example acetonitrile, dimethylformamide, alcohols, aliphatic hydrocarbons, aromatic hydrocarbons, etc.may be used. Alternatively, the carbon tetrahalide may be used as the solvent as well as a reactant, if the carbon tetrahalide is a liquid. When a solvent is used, a polar solvent is preferred since the yield generally is increased thereby. A coordination complex of a metal salt with an electron donor is usually preferred to the salt itself, butylamine being a useful donor, with ferric chloride hexahydrate a preferred salt. When a metal salt or coordination complex is employed as the catalyst, the reaction is generally conducted in the temperature range 50° to 200° C., preferably between about 70° and 150° C.

The coordination complex catalysts retain their activity over a long period of time, and, in addition, can be reused. For these reasons, they are preferred over most free radical catalysts.

Step 3

The process of this invention represented by Step 3 involves the base-induced dehydrohalogenation of the γ-halocarboxylate, B, to produce a dihalovinylcyclopropanecarboxylate, C, via the intermediates X, Y or Z, compositions of matter which are useful in the practice of the process, which may or may not be isolated depending upon the reaction coditions. In the conversion of B to C, 2 moles of acid, HX, are eliminated and the elimination can be made to take place one mole at a time.

The structure of the γ-halocarboxylate, B, will be dictated by the structures of the materials employed in Steps 1, 1' and 2.

For the purposes of the process of Step 3:

$R^2$ and $R^3$ each is a hydrogen atom, a lower alkyl group, a lower alkenyl group, a lower alkynyl group, a lower cycloalkyl group, a phenyl group or an aralkyl group such as benzyl: $R^2$ and $R^3$ together may constitute a lower alkylene chain of at least 2 carbon atoms; and when one of $R^2$ and $R^3$ is other than hydrogen; the other may be a lower alkoxycarbonyl group, a lower alkanoyl group, an aroyl group such as benzoyl, a di(lower alkyl)amide group, or a nitrile group.

$R^4$, $R^5$ and $R^6$ are hydrogen atoms.

$R^7$ is a hydrogen atom, a lower alkyl group, a lower alkenyl group, a lower alkynyl group, a lower cycloalkyl group, a phenyl group, an aralkyl group such as benzyl, a lower alkoxycarbonyl group, a lower alkanoyl group, an aroyl group such as benzoyl, a di(lower alkyl)amide group or a nitrile group.

When it is desired to produce a dihalovinylcyclopropanecarboxylate which may be converted readily into pyrethroid insecticides of the type represented by II and III, the γ-halocarboxylate will be chosen such that $R^4$, $R^5$, $R^6$ and $R^7$ are hydrogen; $R^2$ and $R^3$ are methyl groups and X is chlorine. Among compounds of that type, it has been found that an especially useful and preferred one is the novel compound, ethyl 3,3-dimethyl-4,6,6,6-tetrachlorohexanoate.

The nature and quantity of the base which is used, the solvents, and the temperature determine whether the product of the reaction will be one of the intermediates X, Y or Z, or whether the reaction will proceed all the way to the dihalovinylcyclopropanecarboxylate, C.

If it is desired to produce the dihalovinylcyclopropanecarboxylate, C, directly, anhydrous bases which can be used in the process of Step 3 include sodium hydroxide and potassium hydroxide; alkali metal alkoxides such as sodium ethoxide, sodium methoxide, sodium t-butoxide, potassium t-butoxide, and the like, previously prepared or prepared in situ; sodium hydride, sodium naphthalene and the like; but the use of sodium hydride or an alkali metal alkoxide is preferred. At least 1.5 molar equivalents of the base, preferably 2 to 5 molar equivalents per mole of γ-halocarboxylate should be used. The process can be carried out advantageously in a solvent. Examples of solvents which can be used are alcohols, such as methanol, ethanol, t-butanol, etc., as well as ethers such as diethyl ether, tetrahydrofuran, dimethoxyethane and the like.

It was found that the ratio of cis to trans isomers in the final product can be varied over an unexpected range by simply changing the temperature employed.

For example, when the base-solvent combination is sodium t-butoxide in tetrahydrofuran, and the reaction is conducted at about 0°, the cis:trans ratio is about 50:50; whereas when the reaction is carried out near room temperature from intermediate Y, the cis:trans ratio is approximately 10:90.

To produce directly the dihalovinylcyclopropanecarboxylate, C, from B, the reaction generally may be conducted in the temperature range 50° to 200° C., preferably 60° to 100° C.; but if sodium or potassium t-butoxide and an ethereal solvent such as tetrahydrofuran are utilized, the reaction may be carried out at temperatures as low as −30° C.

To conduct the process of Step 3 so as to stop at intermediate X, the reaction should be conducted at a temperature no higher than about 25° C. in order to avoid the formation of Y, which is produced via X, and it is preferred that the γ-halogen atom in B have a high atomic number, such as bromine or iodine. In general, the use of an aprotic solvent favors the formation of X, and diethyl ether, tetrahydrofuran, dimethylformamide, dimethyl sulfoxide and the like may be employed. Any of the bases specified above to produce the dihalovinylcyclopropanecarboxylate, C, may be used, but the sodium or potassium lower alkoxides, especially ethoxides are preferred. Generally, between 1 and 2 moles of base per mole of γ-halocarboxylate are employed, but about 1.2 moles of base per mole of γ-halocarboxylate is preferred.

To conduct the process of Step 3 such that the intermediate Y is produced from the γ-halocarboxylate, B, a polar aprotic solvent and higher temperatures may generally be employed; an effective combination is sodium ethoxide in dimethylformamide between the temperatures of about 25° and 150° C., with 50° to 150° C. being preferred. Intermediate Y may also be made from intermediate X by heating the latter or by employing an acid in catalytic amounts. The heat-induced isomerization can be carried out at temperatures between about 50° and 200° C. At temperatures below about 50° C. the reaction proceeds slowly, while above 200° C. undesired by-products are formed. The preferred temperature range is 100° to 170° C. Examples of acid catalysts which can be used to effect the isomerization are aliphatic acids such as acetic acid, propionic acid, butyric acid, isobutyric acid and the like; phenols such as phenol, hydroquinone and the like; and Lewis acids such as aluminum chloride, zinc chloride and the like. Protonic acids are generally preferred to Lewis acids since they give higher yields. The acid catalyst is generally employed in amounts ranging from about 0.05 to 10 mole percent of catalyst per mole of X. It is anticipated that the combination of an acid catalyst with thermal treatment will increase the rate of isomerization. It is not necessary that the isomerization be conducted in the presence of a solvent, but, if desired, solvents which do not adversely affect the reaction or the product may be employed; for example, benzene, toluene, xylene, tetralin, petroleum ether, dimethoxyethane, di(methoxyethyl)ether and the like.

The process of Step 3 may also be utilized to prepare the intermediate Z from the γ-halocarboxylate, B. In that case, the base may be either sodium or potassium t-butoxide, preferably in excess with respect to the γ-halocarboxylate. Solvents such as benzene, dioxane, dimethylformamide or tetrahydrofuran may be utilized. t-Butyl alcohol may be used and a mixture with benzene is preferred. The reaction may be carried out successfully at temperatures ranging from about 25° to 50° C.

In any case in which it is desired to produce the dihalovinylcyclopropanecarboxylate, C, from any of the intermediates X, Y or Z, the conditions described above for making C from the γ-halocarboxylate, B, may be employed.

A wide variety of cyclopropanecarboxylates closely related to the dihalovinylcyclopropanecarboxylates may be prepared by the processes of this invention. For example, in Step 2, in place of a carbon tetrahalide, other structurally similar polyhalogenated compounds, including chloroform, bromoform, α,α,α-trihalotoluene, lower trihaloacetates, trihaloacetonitriles, and polyhalogenated lower alkanes, may be added to the olefinic double bond. Such additions will give products analogous to the γ-halocarboxylates described above, but with a substituent other than halogen in the c-position, a substituent such as hydrogen, lower alkyl, lower haloalkyl, phenyl, nitrile, or lower alkoxycarbonyl. These products will undergo dehydrohalogenation and ring closure to form cyclopropanecarboxylates useful as insecticides or in the preparation of insecticides Similarly, intermediates of types X and Y may be prepared with the above-noted substituents other than halogen in the c-position, and these compounds may also be used to prepare β-substituted vinylcyclopropanecarboxylates where a β-substituent is other than halogen. For example, ethyl 4,6-dichloro-3,3-dimethyl-5-hexenoate is reacted with sodium t-butoxide in benzene to form ethyl 2-(β-chlorovinyl)-3,3-dimethylcyclopropanecarboxylate.

Other means of introducing halogen may also be used to prepare compounds capable of undergoing the dehydrohalogenation and ring closure of Step 3. γ-Unsaturated alkenoates may be halogenated in the ε-position with a halogenating agent, for example N-bromosuccinimide (NBS), to form compounds analogous to the X intermediates described above. Such compounds will also undergo dehydrohalogenation and ring closure to form cyclopropanecarboxylates. The reaction sequence is illustrated below:

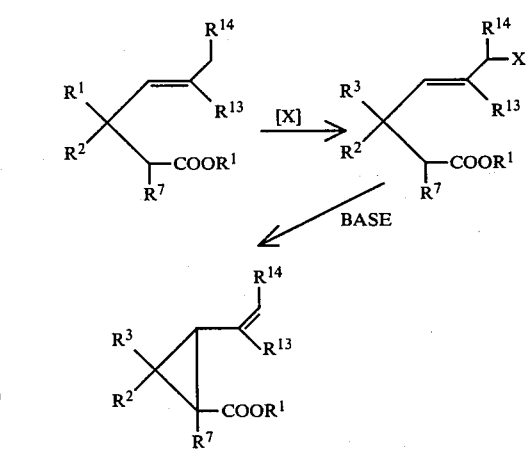

where $R^1$, $R^2$, $R^3$, $R^7$ and X are as previously defined for Step 2, except neither $R^2$ nor $R^3$ is hydrogen; $R^{13}$ and $R^{14}$ are hydrogen, lower alkyl, or phenyl.

The practice of this invention is illustrated further by the additional Examples which follow.

EXAMPLE III

Synthesis of Ethyl 2-(β,β-Dichlorovinyl)-3,3-dimethylcyclopropanecarboxylate

A. Preparation of ethyl 3,3-dimethyl-4-pentenoate

A mixture of 12.9 g (0.15 mole) of 3-methyl-2-buten-1-ol, 48.6 g (0.3 mole) of ethyl orthoacetate and 0.5 g of hydroquinone was heated at 140° for 20 hours with stirring. Ethanol was removed by distillation during the heating. At the end of 20 hours, the mixture was distilled under reduced pressure to give, after removal of unreacted ethyl orthoacetate, 17.6 g (75% yield) of ethyl 3,3-dimethyl-4-pentenoate, b.p. 74°–78°/55 mm.

B. Addition of bromotrichloromethane to ethyl 3,3-dimethyl-4-pentenoate

Fifty milligrams of azobisisobutyronitrile was added to a solution of 1.56 g (0.01 mole) of ethyl 3,3-dimethyl-4-pentenoate in 5 ml of bromotrichloromethane. The mixture was heated for 10 hours at 130°. Unreacted bromotrichloromethane was removed, and the residue was distilled under reduced pressure to give 3.2 g (89% yield) of ethyl 4-bromo-6,6,6-trichloro-3,3-dimethylhexanoate, b.p. 102°–105°/0.1 mm.

Calculated for $C_{10}H_{16}BrCl_3O_2$: C, 33.88; H, 4.55. Found: C, 33.83; H, 4.35.

nmr δ ppm ($CCl_4$): 4.49 (q, 1H), 4.08 (q, 2H), 3.29 (s, 1H), 3.32 (d, 1H), 2.42 (q, 2H), 1.35–1.13 (m, 9H).

C. Simultaneous cyclization and dehydrochlorination

A solution of 709 mg (2 mmoles) of ethyl 4-bromo-6,6,6-trichloro-3,3-dimethylhexanoate in 5 ml of anhydrous tetrahydrofuran was added dropwise to a suspension of 448 mg (4 mmoles) of potassium t-butoxide in 15 ml of tetrahydrofuran and the mixture was heated under reflux for 2 hours. The mixture was then allowed to cool and an additional 220 mg of potassium t-butoxide was added. The mixture was heated under reflux for 1 hour. Then, another 110 mg of potassium t-butoxide was added, and the mixture again was heated under reflux for 1 hour. The mixture was poured into ice water and extracted with diethyl ether. The ether extract was dried over magnesium sulfate, the ether was removed by distillation, and the residue was distilled under reduced pressure to give 330 mg (70% yield) of ethyl 2-(β,β-dichlorovinyl)-3,3-dimethylcyclopropanecarboxylate, b.p. 86°/0.5 mm.

Analysis:

nmrβppm ($CCl_4$):6.22(d,0.5H), 5.56(d,0.5H), 4.05(b.q., 2H), 2.35–1.05 (m, 11H).

ir ($cm^{-1}$):3060, 1730, 1615, 1230, 1182, 1145, 1120, 1087, 925, 860, 817, 790, 765, 702, 650.

EXAMPLE IV

Synthesis of Ethyl 2-(β,β-Dibromovinyl)-3,3-dimethylcyclopropanecarboxylate

A. Addition of carbon tetrabromide to ethyl 3,3-dimethyl-4-pentenoate

Fifty milligrams of azobisisobutyronitrile was adddded to a mixture of 1.56 g (0.01 mole) of ethyl 3,3-dimethyl-4-pentenoate and 3.32 g (0.01 mole) of carbon tetrabromide. The mixture was heated for 5 hours at 120° under an argon atmosphere. The mixture was then allowed to cool and was purified by column chromatography with a silica gel column and a 1:1 mixture of benzene and hexane as the eluting solvent. Concentration of the eluent gave 3 g (60% yield) of ethyl 4,6,6,6-tetrabromo-3,3-dimethylhexanoate.

Analysis: Calculated for $C_{10}H_{16}Br_4O_2$: C,24.62; H,3.31; Br,65.51. Found: C,24.87; H,3.25; Br,65.60.

nmrδppm($CCl_4$): 4.35 (q,1H), 4.07 (q,2H), 3.55 (m,2H), 2.43 (q,2H), 1.40–1.15 (m,9H).

B. Simultaneous cyclization and dehydrobromination

To 1.46 g of ethyl 4,6,6,6-tetrabromo-3,3-dimethylhexanoate in 16 ml of absolute ethanol was added dropwise 5 ml of an ethanol solution containing 0.62 g of sodium ethoxide. The mixture was cooled in ice throughout the addition. The mixture was warmed to room temperature and stirred for 6 hours. An additional 2.5 ml of ethanolic sodium ethoxide (about 0.3 g) was added, and the mixture was stirred for an additional 12 hours. The mixture was then poured into ice water and extracted with diethyl ether. The ether solution was dried over magnesium sulfate and distilled to give 0.77 g (79% yield) of ethyl 2-(β,β-dibromovinyl)-3,3-dimethylcyclopropanecarboxylate, b.p. 98°–101°/0.4 mm.

Analysis:

Calculated for $C_{10}H_{14}Br_2O_2$: C,36.84: H,4.33: Br,49.02. Found: C,37.07: H,4.40: Br,49.27.

nmrδppm ($CCl_4$): 6.12(d,1H), 4.08(q,2H). 2.20–1.40 (m,2H). 1.37–1.10 (m,9H).

ir($cm^{-1}$): 1725, 1223, 1175, 855, 800, 762.

EXAMPLE V

Synthesis of Ethyl 3,3-Dimethyl-1-pentenoate

A. Using phenol as catalyst

A mixture of 43 g (0.5 mole) of 3-methyl-2-buten-1-ol, 97 g (0.6 mole) of ethyl orthoacetate, and 7.0 g (0.075 mole) of phenol was heated at 135°–140° with stirring for 9–10 hours. Ethanol was distilled from the mixture as the reaction proceeded. When the evolution of ethanol had ceased, heating was discontinued and the mixture was allowed to cool to room temperature. The mixture was then dissolved in diethyl ether and the ethereal solution was treated with 1N hydrochloric acid to decompose unreacted ethyl orthoacetate. The ethereal solution was then washed successively with a saturated aqueous solution of sodium bicarbonate and with water, then dried over magnesium sulfate. The dried solution was concentrated and distilled under reduced pressure to give 60.8 g (78% yield) of ethyl 3,3-dimethyl-4-pentenoate, b.p. 57°–60°/11 mm.

Analysis:

nmrδppm($CCl_4$): 6.15–5.60 (d.d. 1H), 5.15–4.68 (m, 2H), 4.02 (q, 2H), 2.19 (s, 2H), 1.45–1.05 (m, 9H).

ir($cm^{-1}$): 3090, 1740, 16:0, 1370, 1240, 1120, 1030, 995, 910.

B. Using boric acid as catalyst

A mixture of 4.3 g of 3-methyl-2-buten-1-ol, 16.2 g of ethyl orthoacetate and 86 mg of boric acid was heated for 2 hours at 120° with stirring, during which ethanol was evolved and removed. The temperature was then increased to 145°–150° where it was maintained for an additional 8 hours. When ethanol evolution ceased, the mixture was distilled to separate unreacted ethyl orthoacetate from 6.25 g (80% yield) of ethyl 3,3-dimethyl-4-pentenoate, b.p. 78°–80°/51 mm.

C. Using phosphoric acid as catalyst

A mixture of 4.3 g of 3-methyl-2-buten-1-ol, 16.2 g of ethyl orthoacetate and 3 drops of phosphoric acid was reacted as described in Example V A to give 6.15 g (79% yield) of ethyl 3,3-dimethyl-4-pentenoate, b.p. 87°–88°/ 58 mm.

D. Using isobutyric acid as catalyst

A mixture of 0.65 g of 3-methyl-2-buten-1-ol, 2.43 g of ethyl orthoacetate and 50 mg of isobutyric acid was treated as described in Example I A. Gas chromatographic analysis of the benzene solution showed that ethyl 3,3-dimethyl-4-pentenoate had been produced in 70% yield.

E. Using mercuric acetate as catalyst

Example I A was repeated, substituting 50 mg of mercuric acetate for the phenol, giving ethyl 3,3-dimethyl-4-pentenoate in 69% yield (based on gas chromatographic analysis).

F. Using hydroquinone as catalyst

Example I A was repeated, substituting 25 mg of hydroquinone for the phenol, giving ethyl 3,3-dimethyl-4-pentenoate in 51% yield (based on gas chromatographic analysis).

G. Without catalyst

A mixture of 4.3 g of 3-methyl-2-buten-1-ol and 8.1 g of ethyl orthoacetate was heated with stirring. The temperature was increased slowly from room temperature to 165° over 2 hours, during which 2.21 g of ethanol was collected. The temperature was maintained at 165° for 26 hours, during which time an additional 1.52 g of ethanol was collected. The reaction mixture was then allowed to cool and diluted with diethyl ether. The ether solution was washed successively with dilute hydrochloric acid, saturated aqueous sodium bicarbonate and saturated aqueous sodium chloride. The washed solution was dried over magnesium sulfate and distilled to give 4.03 g (52% yield) of ethyl 3,3-dimethyl-4-pentenoate, b.p. 80°–85°/52 mm.

H. Via 1,1-diethoxy-1-(3-methyl-2-buten-1-yloxy)-ethane (an Intermediate W)

1. Preparation of 1,1-diethoxy-1-(3-methyl-2-buten-1-yloxy)ethane

A mixture of 4.3 g of 3-methyl-2-buten-1-ol and 16.2 of ethyl orthoacetate was heated with stirring. The temperature was raised slowly over 2 hours to 120°, during which time 1.8 g of ethanol was evolved and removed. Heating was continued at 120° for 30 minutes and the reaction mixture was then distilled to give, after removal of 8.5 g of unreacted ethyl orthoacetate (b.p. 50°–65°/57 mm), 4.25 g of 1,1-diethoxy-1-(3-methyl-2-buten-1-yloxy)ethane, b.p. 75°–76°/6 mm.

Analysis:
Calculated for $C_{11}H_{22}O_3$: C, 65.31; H, 10.96;. Found: C, 65.52; H, 10.74.

2. Preparation of ethyl 3,3-dimethyl-4-pentenoate

A mixture of 2.02 g of 1,1-diethoxy-1-(3-methyl-2-buten-1-yloxy)ethane and 20 mg of phenol was heated for 12 hours at 150°–160°, during which time ethanol was evolved. Distillation of the residue gave 1.12 g (72% yield) of ethyl 3,3-dimethyl-4-pentenoate, b.p. 80°–83°/57 mm.

Similarly, in the absence of phenol, 2.02 g of 1,1-diethoxy-1-(3-methyl-2-buten-1-yloxy)ethane was heated for 20 hours at 150°–160°. Distillation than gave 1.06 g (68% yield) of ethyl 3,3-dimethyl-4-pentenoate, b.p. 87°–89°/62 mm.

EXAMPLE VI

Synthesis of Other γ-Unsaturated Carboxylates

A. Ethyl 2,3,3-trimethyl-4-pentenoate

A mixture of 3.44 g (0.04 mole) of 3-methyl-2-buten-1-ol, 14.08 g (0.08 mole) of ethyl orthopropionate and 0.35 g of phenol was heated at 140° with stirring for 24 hours, the evolved ethanol being collected. The reaction mixture was then distilled to give, after removal of unreacted ethyl orthopropionate, 4.76 g (70% yield) of ethyl 2,3,3-trimethyl-4-pentenoate, b.p. 90°–92°/45 mm.

Analysis:
nmrδppm($CCl_4$): 6.10–5.55 (dd.1H), 5.10–4.70 (m, 2H), 4.05 (q, 2H), 2.25 (q, 1H), 1.22 (t, 3H), 1.20–0.95 (m, 9H).

B. Ethyl 2-methyl-3-phenyl-4-pentenoate

A mixture of 2.68 g of cinnamyl alcohol, 7.04 g of ethyl orthopropionate and 300 mg of phenol was treated as described in Example VI A to give, on distillation, 2.07 g (62% yield) of ethyl 2-methyl-3-phenyl-4-pentenoate, b.p. 104°/1.5 mm.

Analysis:
nmr δ ppm ($CCl_4$): 7.12 (b.s., 5H), 6.30–4.80 (m, 3H), 4.26–3.20 (m, 3H), 3.00–2.50 (m, 1H), 1.40–0.78 (m, 6H).

C. Ethyl 2,3-dimethyl-4-pentenoate

A mixture of 1.44 g of 2-buten-1-ol, 7.04 g of ethyl orthopropionate and 30 mg of boric acid was heated at 120° with stirring for 2 hours. The temperature was then increased to 140° where it was maintained for 20 hours. Distillation gave a mixture of unreacted orthopropionate and the desired product. The distillate was dissolved in diethyl ether. The ethereal solution was washed three times with 1N hydrochloric acid, then successively with saturated aqueous sodium bicarbonate and sodium chloride. The washed ethereal solution was dried over magnesium sulfate and distilled to give 1.64 g (53% yield) of ethyl 2,3-dimethyl-4-pentenoate, b.p. 90°–92°/65 mm.

Analysis:
nmr δ ppm ($CCl_4$): 5.85–5.37 (m, 1H), 5.04–4.78 (m, 2H), 4.02 (q, 2H), 2.56–1.98 (m, 2H), 1.22 (t, 3H), 1.20–0.88 (m, 6H).

D. Methyl 2-ethyl-3,3-dimethyl-4-pentenoate

A mixture of 10.32 g of 3-methyl-2-buten-1-ol, 26.6 g of methyl orthobutyrate and 200 mg of phenol was heated at 120° with stirring for 2 hours. The temperature was then increased to 140° where it was maintained for 23 hours. The mixture was distilled to give, after removal of unreacted ethyl orthobutyrate, 11.55 g (57% yield) of methyl 2-ethyl-3,3-dimethyl-4-pentenoate, b.p. 91°–94°/45 mm.

Analysis: nmr δ ppm ($CCl_4$): 5.78 (d.d.1H), 5.13–4.70 (m, 2H), 3.61 (s, 3H), 2.32–1.98 (m, 1H), 1.90–1.20 (m, 2H), 1.02 (s, 6H), 0.80 (b.t., 3H).

In the same manner the following γ-unsaturated carboxylates were prepared:

E. Ethyl 3-phenyl-4-pentenoate, b.p. 76°–77°/0.2 mm.
F. Ethyl 3-methyl-4-pentenoate, b.p. 85°–89°/63 mm.
G. Ethyl 2,3,3-trimethyl-4-hexenoate, b.p. 97°–99°/37 mm.
H. Ethyl 2,3,3,5-tetramethyl-4-hexenoate, b.p. 115°–117°/40 mm.
I. Ethyl 2,3,3-trimethyl-4-heptenoate, b.p. 120°–122°/45 mm.
J. Ethyl 2,3,3-trimethyl-4-octenoate, b.p. 128°–131°/40 mm.
K. Methyl 2-ethyl-3,3-dimethyl-4-hexenoate, b.p. 97°–100°/30 mm.
L. Ethyl 3,3-dimethyl-4-hexenoate, b.p. 103°–105°/57 mm.
M. Ethyl 3,3-dimethyl-4-heptenoate, b.p. 103°–107°/38 mm.
N. Ethyl 3,3-dimethyl-4-octenoate, b.p. 114°–116°/33 mm.
O. Ethyl 3,3,5-trimethyl-4-hexenoate, b.p. 100°–104°/45 mm.
P. Ethyl 5-cyclopentyl-3,3-dimethyl-4-pentenoate, p.b. 119°–123°/15 mm.
Q. Ethyl 3,3,6-trimethyl-4-heptenoate, b.p. 90°–93°/30 mm.
R. Ethyl 3,3,5-trimethyl-4-heptenoate, b.p. 100°–104°/20 mm.
S. Benzyl 3,3-dimethyl-4-pentenoate In the manner of Example I B, 810 mg of benzyl alcohol was reacted with 1122 mg of ethyl 3,3-dimethyl-4-pentenoate in the presence of 48 mg of sodium ethoxide in 30 ml of toluene to give 1.0 g (65% yield) of benzyl 3,3-dimethyl-4-pentenoate, b.p. 92°–98°/0.1 mm.
Analysis:
Calculated for $C_{14}H_{18}O_2$: C, 76.49; H, 8.51. Found: C, 76.79; H, 8.25.
nmr δ ppm ($CCl_4$): 7.29 (b.s., 5H), 5.84 (d.d., 1H), 5.03 (s, 2H), 5.05–4.70 (m, 2H), 2.22 (s, 2H), 1.06 (s, 6H).

T. Using similar techniques, the following γ-unsaturated carboxylates can be prepared:
1. isopropyl 2-benzyl-3,3-dimethyl-4-pentenoate
2. t-butyl 3,3-dimethyl-4-pentenoate
3. ethyl 2-cyclopentyl-4-pentenoate
4. ethyl 3-ethyl-3-methyl-4-pentenoate
5. ethyl 3-ethyl-3-isopropyl-4-pentenoate
6. ethyl 3-t-butyl-3-propyl-4-pentenoate
7. ethyl 3-methyl-3-vinyl-4-pentenoate
8. ethyl 3-(2-butenyl)-3-ethyl-4-pentenoate
9. ethyl 2-(1-vinylcyclohexyl)acetate
10. ethyl 3-(2-butynyl)-3-methyl-4-pentenoate
11. ethyl 3-cyclohexyl-3-methyl-4-pentenoate
12. ethyl 3-benzyl-3-methyl-4-pentenoate
13. ethyl 2-benzoyl-3-carbethoxy-4-pentenoate
14. ethyl 3-acetyl-4-pentenoate
15. ethyl 3-benzoyl-4-pentenoate
16. ethyl 3-(N,N-dimethylcarboxamido)-4-pentenoate
17. ethyl 3-(N-ethyl-N-isopropylcarboxamido)-4-pentenoate
18. ethyl 3-cyano-2-ethynyl-4-pentenoate
19. ethyl 3-chloromethyl-4-pentenoate
20. ethyl 3-(2-bromoethyl)-4-pentenoate
21. ethyl 3-(1-fluoro-1-methylethyl)-4-pentenoate
22. ethyl 3,3-diphenyl-4-pentenoate
23. ethyl 5-allyl-3,3-dimethyl-4-hexenoate
24. ethyl 3,3-dimethyl-5-phenyl-4-pentenoate
25. methyl 5-cyclohexyl-4-pentenoate
26. ethyl 4-cyclohexylidene-3,3-dimethylbutanoate
27. ethyl 5-carbomethoxy-3,3-dimethyl-4-pentenoate
28. ethyl 5-(2-butynyl)-3,3-dimethyl-4-pentenoate
29. ethyl 5-acetyl-3,3-dimethyl-4-pentenoate
30. ethyl 5-benzyl-3,3-dimethyl-4-pentenoate
31. ethyl 3,3-dimethyl-5-(N,N-dimethylcarboxamido)-4-pentenoate
32. ethyl 5-cyano-3,3-dimethyl-4-pentenoate
33. ethyl 5-benzoyl-3,3-dimethyl-4-pentenoate
34. ethyl 5-(2-bromoethyl)-3,3-dimethyl-4-pentenoate
35. ethyl 2,2,3,3-tetramethyl-4-pentenoate
36. ethyl 2,3,3-trimethyl-2-isopropyl-4-pentenoate
37. ethyl 2-chloromethyl-2-phenyl-4-pentenoate
38. ethyl 3,3-dimethyl-2,2-diphenyl-4-pentenoate
39. ethyl 2-carbomethoxy-3,3-dimethyl-4-pentenoate
40. ethyl 2-acetyl-3,3-dimethyl-4-pentenoate
41. ethyl 2-butyryl-3,3-dimethyl-4-pentenoate
42. ethyl 3,3-dimethyl-2-(N,N-dimethylcarboxamido)-4-pentenoate
43. ethyl 2-cyano-3,3-dimethyl-4-pentenoate
44. ethyl 1-allyl-1-cyclohexanecarboxylate
45. methyl 2-cyano-3-ethyl-4-heptenoate
46. isopropyl 5-chloromethyl-2-vinyl-4-pentenoate
47. methyl 3-cyano-2-(N,N-dimethylcarboxamido)-5-(2-fluoroethyl)-4-hexenoate

EXAMPLE VII

Synthesis of Ethyl 4,6,6,6-Tetrahalo-3,3-dimethylhexanoates by Addition of Carbon Tetrahalides to Ethyl 3,3-Dimethyl-4-pentenoate A. Addition of carbon tetrachloride in the presence of ferric chloride, butylamine and acetonitrile Example II A was repeated except that the dimethylformamide was replaced by 1.23 g of acetonitrile, producing 2.54 g (82% yield) of ethyl 4,6,6,6-tetrachloro-3,3-dimethylhexanoate.

B. Addition of carbon tetrachloride in the presence of ferric chloride and butylamine without added solvent Example II A was repeated, omitting the dimethylformamide, to give 2.23 g (72% yield) of ethyl 4,6,6,6-tetrachloro-3,3-dimethylhexanoate.

C. Addition of carbon tetrabromide in the presence of ferric chloride, butylamine and dimethylformamide A mixture of 135.2 mg (0.5 mmole) of ferric chloride hexahydrate, 146.3 mg (2.0 mmoles) of n-butylamine, 2.19 g of dimethylformamide, 1.56 g (10 mmoles) of ethyl 3,3-dimethyl-4pentenoate, and 3,32 g (10 mmoles) of carbon tetrabromide in a sealed tube was heated for 20 hours at 120°. The tube was allowed to cool and the contents were diluted with chloroform. The chloroform solution was washed successively with 1N hydrochloric acid, saturated aqueous sodium bicarbonate and water. The washed chloroform solution was dried over magnesium sulfate and distilled to give 2.9 g (60% yield) of ethyl 4,6,6,6-tetrabromo-3,3-dimethylhexanoate, b.p. 144°/0.2 mm.

D. Addition of bromotrichloromethane in the presence of ferric chloride, butylamine and dimethylformamide Example VII C was repeated using 2.0 g (10 mmoles) of bromotrichloromethane instead of carbon tetrabromide to obtain 3.1 g (70% yeild) of ethyl 4-bromo-6,6,6-trichloro3,3-dimethylhexanoate, b.p. 128°/0.25 mm.

E. Addition of carbon tetrachloride in the presence of ferric chloride, butylamine and dimethylformamide A mixture of 94.5 mg (0.35 mmole) of ferric chloride hexahydrate, 102 mg (1.4 mmole) of butylamine, 1.2 ml of dimethylformamide, 780 mg (5mmoles) of ethyl 3,3-dimethyl-4-pentenoate, and 1.54 g (10 mmoles) of carbon tetrachloride in a sealed tube was heated for 15 hours at 120°. The contents of the tube was cooled to room temperature and diluted with carbon tetrachloride to a final volume of 5 ml. Gas chromatographic analysis of the solution showed that ethyl 4,6,6,6-tetrachloro-3,3-dimethylhexanoate had been produced in 95% yield.

F. Addition of carbon tetrachloride in the presence of ferrous chloride, butylamine and dimethylformamide Example VII E was repeated using 74.7 mg (0.25 mmole) of ferrous chloride instead of ferric chloride. Gas chromatographic analysis showed an 82% yield of ethyl 4,6,6,6-tetrachloro-3,3-dimethylhexanoate.

Example VII E was repeated using the following catalysts instead of ferric chloride to produce ethyl 4,6,6,6-tetrachloro-3,3-dimethylhexanoate in the stated yields:

G. Cuprous chloride—76% yield
H. Cupric cyanide—72% yield

I. Ethanol as solvent

Repetition of Example VII E using 690 mg of absolute ethanol instead of the dimethylformamide resulted in an 80% yield of ethyl 4,6,6,6-tetrachloro-3,3-dimethylhexanoate.

J. Addition of carbon tetrachloride in the presence of benzoyl peroxide

A mixture of 3.12 g (0.02 mole) of ethyl 3,3-dimethyl-4-pentenoate, 30 ml of carbon tetrachloride, and 50 mg of benzoyl peroxide in a pressure vessel was heated for 4 hours at 140°. The vessel was cooled, an additional 50 mg of benzoyl peroxide was added and the vessel was again heated at 140° for 4 hours. After cooling to room temperature, the mixture was washed successively with saturated aqueous sodium bicarbonate and water. The mixture was dried over magnesium sulfate and distilled to give 4.56 g (74% yield) of ethyl 4,6,6,6-tetrachloro-3,3-dimethylhexanoate, b.p. 107°–108°/0.3 mm.

K. Photocatalyzed addition of carbon tetrabromide

A mixture of ethyl 3,3-dimethyl-4-pentenoate (0.78 g) and carbon tetrabromide (3.32 g), continuously purged with argon, was irradiated with a 200 watt visible light source for 10 hours at room temperature. The resulting dark-brown oil was purified by column chromatography to afford 1.46 g (59.8% yield) of ethyl 4,6,6,6-tetrabromo-3,3-dimethylhexanoate.

EXAMPLE VIII

Addition of Carbon Tetrahalides to Other γ-Unsaturated Carboxylates

A. Ethyl 4,6,6,6-tetrachloro-2,3,3-trimethylhexanoate

1. Using benzoyl peroxide

A mixture of 1.36 g (8 mmoles) of ethyl 2,3,3-trimethyl-4-pentenoate, 20 ml of carbon tetrachloride, and 50 mg of benzoyl peroxide was charged into a pressure vessel. The vessel was purged with argon, sealed and heated for 5 hours at 130°–140°. At 5-hour intervals thereafter, the vessel was cooled, an additional 50 mg of benzoyl peroxide was added, the reactor was repurged, resealed, and heating was continued until a total of 200 mg of benzoyl peroxide had been added and 20 hours heating time had elapsed. The mixture was allowed to cool, then was washed successively with saturated aqueous sodium bicarbonate and saturated aqueous sodium chloride, then dried over magnesium sulfate. Distillation gave 1.81 g (70% yield) of ethyl 4,6,6,6-tetrachloro-2,3,3-trimethylhexanoate, b.p. 106°–107°/0.3 mm.

Analysis:

nmr δ ppm (CCl$_4$): 4.43–3.85 (m, 3H), 3.45–3.00 (m, 2H), 2.97–2.63 (m, 1H), 1.35–0.95 (m, 12H).

2. Using ferric chloride, butylamine and dimethylformamide

A mixture of 1.7 g of ethyl 2,3,3-trimethyl-4-pentenoate, 3.08 g of carbon tetrachloride, 190 mg of ferric chloride hexahydrate, 205 mg of n-butylamine, and 2.2 g of dimethylformamide was charged into a pressure vessel. The vessel was purged with argon, sealed and heated for 10 hours in a bath maintained at 120°. The vessel was allowed to cool to room temperature, and the contents were diluted with diethyl ether. The ether solution was washed successively with water, 1N hydrochloric acid, saturated aqueous sodium bicarbonate and water, then dried over magnesium sulfate. The dried solution was distilled to give 1.6 g (49% yield) of ethyl 4,6,6,6-tetrachloro-2,3,3-trimethylhexanoate, b.p. 123°–124°/1.0 mm.

B. Ethyl 4,6,6,6-tetrachloro-3-methylhexanoate

1. Using benzoyl peroxide

A mixture of 2.84 g of ethyl 3-methyl-4-pentenoate, 10 ml of carbon tetrachloride, and 5 mg of benzoyl peroxide was reacted as described in Example VIII A.1, a total of 20 mg of benzoyl peroxide being added during the 20 hours. Distillation of the washed reaction mixture gave 3.79 g (63% yield) of ethyl 4,6,6,6-tetrachloro-3-methylhexanoate, b.p. 103°–105°/0.4 mm.

Analysis:

nmr δ ppm (CCl$_4$): 4.60–4.30 (m, 1H), 4.11 (q, 2H), 3.25–3.00 (m, 2H), 2.75–2.10 (m, 3H), 1.26 (t, 3H), 1.22–0.95 (m, 3H).

2. Using ferric chloride, butylamine and dimethylformamide

Example VIII A.2 was repeated, using 1.42 g of ethyl 3-methyl-4-penteneate instead of the ethyl 2,3,3-trimethyl-4-pentenoate, to give 1.19 g (40% yield) of ethyl 4,6,6,6-tetrachloro-3-methylhexanoate, b.p. 110°/0.7 mm.

C. Ethyl 4-bromo-6,6,6-trichloro-2,3,3-trimethylhexanoate

A mixture of 1.70 g (0.01 mole) of ethyl 2,3,3-trimethyl-4-pentenoate, 5 ml of bromotrichloromethane, and 50 mg of benzoyl peroxide was refluxed vigorously for 10 hours in an argon atmosphere. The mixture was then distilled to give 3.0 g (81% yield) of ethyl 4-bromo-6,6,6-trichloro-2,3,3-trimethylhexanoate, b.p. 115°–120°/0.5 mm Analysis:

nmr δ ppm (CCl$_4$): 4.60–3.80 (m, 3H), 3.70–3.10 (m, 2H), 3.10–2.70 (m, 1H), 1.60–0.95 (m, 12H).

D. Ethyl 4-bromo-6,6,6-trichloro-3-methylhexanoate

A mixture of 2.84 g of ethyl 3-methyl-4-pentenoate, 5 ml of bromotrichloromethane and 5 mg of benzoyl peroxide was refluxed vigorously for 6 hours in an argon atmosphere. Then the mixture was cooled, an additional 5 mg of benzoyl peroxide was added and heating continued. After a total of 12 hours, the mixture was cooled, washed successively with water, saturated aqueous sodium bicarbonate, and water. After drying over magnesium sulfate, the mixture was distilled to give 3.74 g (55% yield) of ethyl 4-bromo-6,6,6-trichloro-3-methylhexanoate, b.p. 110°–113°/0.5 mm.

Analysis:

nmr $\delta$ ppm (CCl$_4$): 4.65–4.35 (m, 1H), 4.14 (q, 2H), 3.45–3.10 (m, 2H), 2.65–2.10 (m, 3H), 1.24 (t, 3H), 1.25–0.95 (m, 3H).

E. Ethyl 4,6,6,6-tetrachloro-2,3-dimethylhexanoate

A mixture of 1.56 g of ethyl 2,3-dimethyl-4-pentenoate, 20 ml of carbon tetrachloride, and 20 mg of benzoyl peroxide was charged into a pressure vessel. The vessel was purged with argon, sealed and heated at 140°. After 8 hours, the reactor was cooled, an additional 10 mg of benzoyl peroxide was added, heating was resumed for an additional 8 hours, 10 mg of benzoyl peroxide was again added and heating was then continued for a total of 24 hours. When the reactor had cooled, the contents were washed successively with saturated aqueous sodium bicarbonate, saturated aqueous sodium chloride and then dried over magnesium sulfate. The dried solution was distilled to give 1.95 g (63% yield) of ethyl 4,6,6,6-tetrachloro-2,3-dimethylhexanoate, b.p. 95°–98°/0.3 mm.

Analysis:

nmr $\delta$ ppm (CCl$_4$): 4.52–4.20 (m, 1H), 4.06 (b.q., 2H), 3.20–3.00 (m, 2H), 2.75–1.82 (m, 2H), 1.40–0.91 (m, 9H).

In the manner of Example VIII A were prepared:

Ethyl 4,6,6,6-tetrachloro-3-phenylhexanoate, b.p. 143°–145°/0.3 mm.

Analysis: nmr $\delta$ ppm (CCl$_4$): 7.50–7.15 (m, 5H), 4.85–4.34 (m, 1H), 4.33–3.80 (m, 2H), 3.78–3.42 (m, 1H), 3.40–2.60 (m, 4H), 1.37–0.95 (m, 3H).

Ethyl 4,6,6,6-tetrachloro-2-methyl-3-phenylhexanoate b.p. 160°–165°/1.0 mm.

Analysis:

nmr $\delta$ ppm (CCl$_4$): 7.45–7.00 (m, 5H), 4.75–4.30 (m, 1H), 4.22–2.20 (m, 6H), 1.42–0.64 (m, 6H).

H. Methyl 4,6,6,6-tetrachloro-2-ethyl-3,3-dimethylhexanoate b.p. 93°–97°/0.2 mm.

Analysis:

nmr $\delta$ ppm (CCl$_4$): 4.10 (d.d, 1H), 3.67 (s, 3H), 3.45–2.30 (m, 3H), 1.95–1.20 (m, 2H), 1.20–0.70 (m, 9H).

I. Benzyl 4,6,6,6-tetrachloro-3,3-dimethylhexanoate

A pressure vessel was charged with 436 mg of benzyl 3,3-dimethyl-4-pentenoate in 618 mg of carbon tetrachloride, followed by a mixture of 440 mg of dimethylformamide, 38 mg of ferric chloride hexahydrate and 41 mg of butylamine. The reactor was purged with argon, closed and heated for 8 hours at 120°. The vessel was allowed to cool and the contents were diluted by addition of 50 ml of diethyl ether. The ether solution was washed successively with water, 1N hydrochloric acid, water, saturated aqueous sodium bicarbonate and water. The washed solution was dried over magnesium sulfate and the solvent was removed under reduced pressure. The residue was purified by column chromatography using a silica gel column with benzene as the eluting solvent to give 470 mg (63% yield) of benzyl 4,6,6,6-tetrachloro-3,3-dimethylhexanoate.

Calculated for C$_{15}$H$_{18}$Cl$_4$O$_2$: C, 48.42; H, 4.88; Cl, 38.11;. Found: C, 48.69; H, 5.13; Cl, 38.42. nmr $\delta$ ppm (CCl$_4$): 7.22 (b.s., 5H), 4.98 (s, 2H), 4.31 (d.d., 1H), 3.32–2.80 (m, 2H), 2.58 (d, 1H), 2.28 (d, 1H), 1.17 (s, 3H), 1.08 (s, 3H)

J. Using similar techniques, the following compounds can be prepared:

1. ethyl 4,6,6,6-tetrachlorohexanoate
2. ethyl 4,6,6,6-tetrachloro-3-ethyl-3-methylhexanoate
3. ethyl 4,6,6,6-tetrachloro-3-ethyl-3-isopropylhexanoate
4. ethyl 3-t-butyl-4,6,6,6-tetrachloro-3-propylhexanoate
5. ethyl 4,6,6,6-tetrachloro-3,3-diphenylhexanoate
6. ethyl-2-[1-(1,3,3,3-tetrachloropropyl)cyclohexyl]acetate
7. ethyl 4,6,6,6-tetrachloro-3-cyclobutylhexanoate
8. methyl 3-benzyl-4,6,6,6-tetrachlorohexanoate
9. isopropyl 3-benzoyl-4,6,6,6-tetrachlorohexanoate
10. ethyl 3-carbethoxy-4,6,6,6-tetrachlorohexanoate
11. ethyl 3-acetyl-4,6,6,6-tetrachlorohexanoate
12. ethyl 3-butyry.-4,6,6,6-tetrachlorohexanoate
13. ethyl 4,6,6,6-tetrachloro-3-(N,N-dimethylcarboxamido)hexanoate
14. ethyl 4,6,6,6-tetrachloro-3-(N-ethyl-N-isopropylcarboxamido)hexanoate
15. ethyl 3-cyano-4,6,6,6-tetrachlorohexanoate
16. ethyl 4,6,6,6-tetrachloro-3-chloromethylhexanoate
17. ethyl 2-benzyl-3-(2-bromoethyl)-4,6,6,6-tetrachlorohexanoate
18. ethyl 4,6,6,6-tetrachloro-3-(1-fluoro-1-methylethyl)hexanoate
19. ethyl 2-benzyl-4-bromo-6,6,6-trichlorohexanoate
20. methyl 6,6,6-trichloro-2-cyclohexyl-4-iodohexanoate
21. ethyl 4,6-dichloro-6,6-difluorohexanoate
22. methyl 4-bromo-6,6,6-trichloro-2,2,3,3-tetramethylhexanoate
23. methyl 4-bromo-6,6,6-trichloro-2-isopropyl-2,3,3-trimethylhexanoate
24. isopropyl 6,6,6-trichloro-4-iodo-2-phenylhexanoate
25. isopropyl 6,6-dichloro-6-fluoro-4-iodo-3-methyl-2,2-diphenylhexanoate
26. ethyl 2-carbomethoxy-4,6,6,6-tetrachlorohexanoate
27. ethyl 2-acetyl-4,6,6,6-tetrachloro-3,3-dimethylhexanoate
28. ethyl 2-butyryl-4,6,6,6-tetrachloro-3,3-dimethylhexanoate
29. ethyl 4,6,6,6-tetrachloro-2-(N,N-dimethylcarboxamido)hexanoate
30. ethyl 4,6-dibromo-2-cyano-6,6-difluoro-3,3-dimethylhexanoate
31. ethyl 1-(2-bromo-4,4,4-trichloro-1,1-dimethylbutyl)-1-cyclohexanecarboxylate
32. t-butyl 4-bromo-6,6,6-trichloro-2-cyano-3-ethylhexanoate

Example IX

Direct Synthesis of Ethyl 2-(β,β-Dichlorovinyl)-3,3-dimethylcyclopropanecarboxylate from Ethyl 4,6,6,6-Tetrachloro-3,3-dimethylhexanoate

A. Using potassium t-butoxide in tetrahydrofuran

A solution of 1.8 g (5.8 mmoles) of ethyl 4,6,6,6-tetrachloro-3,3-dimethylhexanoate in 2 ml of anhydrous tetrahydrofuran was added dropwise to a suspension of 1.3 g (11.6 mmoles) of potassium t-butoxide in 20 ml of anhydrous tetrahydrofuran. The mixture was stirred for 1 hour at room temperature. An additional 0.65 g (5.8 mmoles) of potassium t-butoxide was then added and the mixture was heated under reflux for 2 hours. The mixture was allowed to cool, poured into ice water, and the aqueous mixture was extracted with diethyl ether. After drying over magnesium sulfate, the ether solution was distilled to give 0.93 g (68% yield) of ethyl 2-(β,β-dichlorovinyl)3,3dimethylcyclopropanecarboxylate, b.p, 70°–72°/0.1 mm.

B. Using sodium t-butoxide in tetrahydrofuran

A suspension of 2.11 g (0.011 mole) of sodium t-butoxide in 40 ml of anhydrous tetrahydrofuran was cooled to 0° and to the cold suspension was added dropwise a solution of 1.55 g (0.005 mole) of ethyl 4,6,6,6-tetrachloro-3,3-dimethylhexanoate in 10 ml of anhydrous tetrahydrofuran. When the addition was complete, the mixture was stirred for 2 hours at about 0°. The cold mixture was neutralized by the addition of a diethyl ether solution of hydrogen chloride. The solution was filtered and the filtrate diluted with diethyl ether. The ether solution was washed with water, dried over magnesium sulfate and distilled to give 1.08 g (91% yield) of a mixture of cis and trans ethyl 2-(β,β-dichlorovinyl)-3,3-dimethylcyclopropanecarboxylate, b.p. 63°–66°/0.2 mm. The cis:trans ratio was found by nmr spectroscopic analysis to be 1:1.

C. Using sodium in ethanol

To a cold solution of 1.01 g (44 mmoles) of sodium in 80 ml of absolute ethanol was added dropwise, while cooling with ice, 20 ml of an ethanol solution containing 6.2 g (20 mmoles) of ethyl 4,6,6,6-tetrachloro-3,3-dimethylhexanoate. After the addition, the mixture was stirred for 1 hour at room temperature, then heated under reflux for 0.5 hour. The mixture was then cooled to 0° and neutralized by the dropwise addition of hydrogen chloride in ethanol. The neutral mixture was filtered, and the filtrate concentrated to one-tenth its original volume. The concentrated mixture was diluted with diethyl ether, and the ethereal solution was washed successively with saturated aqueous sodium bicarbonate and sodium chloride. The washed solution was dried over magnesium sulfate and distilled to give 4.47 g (94% yield) of ethyl 2-(β,β-dichlorovinyl)-3,3-dimethylcyclopropanecarboxylate, b.p. 72°–74°/0.4 mm. The cis:trans distribution was found by gas chromatographic analysis to be 34% cis, 66% trans.

D. Using potassium in ethanol

Twenty milliliters of a solution containing 3.10 g (10 mmoles) of ethyl 4,6,6,6-tetrachloro-3,3-dimethylhexanoate in absolute ethanol was added dropwise, with cooling, to a cold solution of 860 mg (22 mmoles) of potassium in 80 ml of absolute ethanol. When the addition was complete, the mixture was stirred for 1 hour at room temperature, then heated under reflux for 0.5 hour. The mixture was treated as described in Example IX C to produce 2.30 g (96% yield) of ethyl 2-(β,β-dichlorovinyl)-3,3-dimethylcyclopropanecarboxylate which was shown by gas chromatographic analysis to be 26% cis, 74% trans.

E. Using sodium in methanol

Example IX D was repeated using a solution of 575 mg (25 mmoles) of sodium in 80 ml of absolute methanol, to which was added 20 ml of a solution of 3.1 g (10 mmoles) of ethyl 4,6,6,6-tetrachloro-3,3-dimethylhexanoate in absolute methanol. The product was 2.09 g (93% yield) of methyl 2-(β,β-dichlorovinyl)-3,3-dimethylcyclopropanecarboxylate, b.p. 68°–70°/0.2 mm, which was found by gas chromatographic analysis to be 23% cis, 77% trans.

F. Using potassium in methanol

Example IX D was repeated using a solution of 860 mg (22 mmoles) of potassium in 80 ml of absolute methanol, to which was added 20 ml of a solution of 3.1 g (10 mmoles) of ethyl 4,6,6,6-tetrachloro-3,3-dimethylhexanoate in absolute methanol. The product was 2.13 g (95% yield) of methyl 2-(β,β-dichlorovinyl)-3,3-dimethylcyclopropanecarboxylate which was found by gas chromatographic analysis to be 25% cis, 75% trans.

EXAMPLE X

Synthesis of Ethyl 6,6,6-Trichloro-3,3-dimethyl-4-hexenoate (an Intermediate X)

Two milliliters of a solution of anhydrous tetrahydrofuran containing 709 mg (2 mmoles) of ethyl 4-bromo-6,6,6-trichloro-3,3-dimethylhexanoate was added dropwise to a suspension of 163 mg (2.4 mmoles) of sodium ethoxiae in 20 ml of anhydrous tetrahydrofuran. The mixture was stirred at room temperature for about 16 hours, poured into ice water and extracted with diethyl ether. The extract was dried over magnesium sulfate and then distilled to give 448 mg (82% yield) of ethyl 6,6,6-trichloro-3,3-dimethyl-4-hexenoate, b.p. 83°–85°/0.1 mm.

Analysis: Calculated for $C_{10}H_{15}Cl_3O_2$: C, 43.90; H, 5.53; Cl, 38.87.

Found: C, 44.12; H, 5.35; Cl, 38.11.

nmr δ ppm (CCl$_4$): 6.13 (q, 2H), 4.07 (q, 2H), 2.29 (s, 2H), 1.50–1.00 (m, 9H).

EXAMPLE XI

Synthesis of Ethyl 4,6,6-Trichloro-3,3-dimethyl-5-hexenoate (an Intermediate Y)

A. From ethyl 4,6,6,6-tetrachloro-3,3-dimethylhexanoate

1. Using sodium ethoxide

A solution of 2.04 g of sodium ethoxide in 60 ml of dimethylformamide was added to a hot solution (140°) of 3.1 g of ethyl 4,6,6,6-tetrachloro-3,3-dimethylhexanoate in 20 ml of dimethylformamide. The mixture was maintained at 140° for 2 hours, then cooled to 0°, neutralized with dry hydrogen chloride and poured into ice water. The aqueous mixture was extracted with ether, and the extract was washed successively with saturated aqueous sodium bicarbonate and sodium chloride. The washed extract was dried over magnesium sulfate and distilled to give 1.81 g (77% yield) of ethyl 4,6,6-trichloro-3,3-dimethyl-5-hexenoate, b.p. 98°–101°/0.6 mm.

2. Using 1,5-diazabicyclo[3.4.0]nonene-5

A solution of 1.42 g of ethyl 4,6,6,6-tetrachloro-3,3-dimethylhexanoate in 10 ml of anhydrous dimethylformamide was added dropwise over 0.5 hour to a stirred solution of 1.58 g of 1,5-diazabicyclo[3.4.0]nonene-5 in 10 ml of anhydrous dimethylformamide maintained at 0°. The mixture was stirred for an additional 2 hours, without cooling, poured into ice water, and the aqueous mixture was extracted with diethyl ether. The ether extract was washed with water, dried over magnesium sulfate and distilled to give a liquid, b.p. 87°–90°/0.12 mm, found by nmr spectral analysis to consist of 800 mg of ethyl 4,6,6-trichloro-3,3-dimethyl-5-hexenoate and 160 mg of ethyl 6,6,6-trichloro-3,3-dimethyl-4-hexenoate. The combined yield was 88%.

B. By rearrangement of ethyl 6,6,6-trichloro-3,3-dimethyl-4-hexenoate (an Intermediate X)

1. By heating in tetralin

A solution of 547 mg (2 mmoles) of ethyl 6,6,6-trichloro-3,3-dimethyl-4-hexenoate in 2ml of etralin was heated at 150° for 24 hours under an argon atmosphere, then distilled to give 356 mg (65% yield) of ethyl 4,6,6-trichloro-3,3-dimethyl-5-hexenoate, b.p. 88°–90°/0.2 mm.

Analysis: Calculated for $C_{10}H_{15}Cl_3O_2$: C, 43.90; H, 5.53; Cl, 38.87.; Found: C, 44.18; H, 5.39; Cl, 38.65.

nmr δ ppm (CCl$_4$): 5.96 (d, 1H), 4.85 (d, 1H), 4.06 (q, 2H), 2.41 (d, 1H), 2.23 (d, 1H), 1.23 (t, 3H), 1.11 (s, 6H). ir (KBr, cm$^{-1}$): 1735, 1613.

2. By heating in bis(2-methoxyethyl)ether

A solution of 547 mg (2 mmoles) of ethyl 6,6,6-trichloro-3,3-dimethyl-4-hexenoate in 2 ml of bis(2-methoxyethyl)ether (diglyme) was treated as in Example X B.1 to give 383 mg (70% yield) of ethyl 4,6,6-trichloro-3,3-dimethyl-5-hexenoate.

3. Heat alone

Ethyl 6,6,6-trichloro-3,3-dimethyl-4-hexenoate (547 mg) was heated at 150° for 10 hours under an argon atmosphere, then distilled to give 246 mg (45% yield) of ethyl 4,6,6-trichloro-3,3-dimethyl-5-hexenoate, b.p. 84°–85°/0.09 mm.

4. Using isobutyric acid

A solution of 547 mg (2 mmoles) of ethyl 6,6,6-trichloro-3,3-dimethyl-4-hexenoate and 30 mg of isobutyric acid in 2 ml of xylene was refluxed for 6 hours under an argon atmosphere, then distilled to give 416 mg (76% yield) of ethyl 4,6,6-trichloro-3,3-dimethyl-5-hexenoate, b.p. 85°–86°/0.1 mm.

5. Using aluminum chloride

A mixture of 274 mg of ethyl 6,6,6-trichloro-3,3-dimethyl-4-hexenoate and 30 mg of aluminum chloride was stirred at room temperature for 24 hours. The mixture was found by gas chromatographic analysis to contain 30% ethyl 4,6,6-trichloro-3,3-dimethyl-5-hexenoate.

EXAMPLE XII

Synthesis of Ethyl 2-(β, β, β-Trichloroethyl)-3,3-dimethylcyclopropanecarboxylate (an Intermediate Z)

A. From ethyl 4,6,6,6-tetrachloro-3,3-dimethylhexanoate

A solution of sodium t-butoxide was prepared by dissolving 280 mg of sodium in a mixture of 60 ml of t-butanol and 30 ml of benzene while protecting the mixture from moisture. To this solution was added, a room temperature, 3.1 g (0.01 mole) of ethyl 4,6,6,6-tetrachloro-3,3-dimethylhexanoate and the mixture was stirred for 2 hours. Excess dry hydrogen chloride was added, the mixture was diluted with water and extracted with diethyl ether. The ether extract was washed successively with saturated aqueous sodium bicarbonate and sodium chloride. The washed extract was dried over magnesium sulfate and distilled to give 2.03 g (74% yield) of ethyl 2-(β,β,β-trichloroethyl)-3,3-dimethylcyclopropanecarboxylate, b.p. 78°–80°/0.1 mm.

Analysis:
Calculated for $C_{10}H_{15}Cl_3O_2$: C, 43.90; H, 5.53; Cl, 38.87. Found: C, 43.80; H, 5.41; Cl, 38.87.

nmr δ ppm (CCl$_4$): 4.03 (d.q. 2H), 3.1–2.7 (m, 2H), 2.1–1.5 (m, 2H), 1.35 (s, 6H), 1.34 (d.t, 3H).

B. From ethyl 4-bromo-6,6,6-trichloro-3,3-dimethylhexanoate

To a solution of 46 mg of sodium in a mixture of 12ml of t-butanol and 6 ml of benzene was added, at room temperature, 709 mg of ethyl 4-bromo-6,6,6-trichloro-3,3-dimethylhexanoate. The mixture was treated as described in Example XII A to produce 470 mg (86% yield) of ethyl 2-(β,β,β-trichloroethyl)-3,3-dimethylcyclopropanecarboxylate.

EXAMPLE XIII

Synthesis of Ethyl 2-(β,β-Dichlorovinyl)-3,3-dimethylcyclopropanecarboxylate From Intermediates X, Y and Z A. From ethyl 6,6,6-trichloro-3,3-dimethyl-4-hexenoate (an Intermediate X)

A solution of 410 mg of ethyl 6,6,6-trichloro-3,3-dimethyl-4-hexenoate in 1.5 ml of anhydrous tetrahydrofuran was added dropwise with stirring to a suspension of 202 mg of potassium t-butoxide in 20 ml of anhydrous tetrahydrofuran. The mixture was heated under reflux with stirring for 3 hours, then poured into ice water. The aqueous mixture was extracted with diethyl ether; the ether extract was dried over magnesium sulfate and distilled to give 281 mg (79% yield) of ethyl 2-(β,β-dichlorovinyl)-3,3-dimethylcyclopropanecarboxylate, b.p. 72°–74°/0.2 mm.

B. From ethyl 4,6,6-trichloro-3,3-dimethyl-5hexenoate (an Intermediate Y)

1. Using sodium in ethanol

A solution of 547 mg (2 mmoles) of ethyl 4,6,6-trichloro-3,3-dimethyl-5-hexenoate in 2 ml of ethanol was added dropwise with stirring to a solution of 57 mg (2.5 mmoles) of sodium in 10 ml of absolute ethanol. The mixture was stirred at room temperature for 5 hours, cooled with ice and then neutralized by adding a solution of hydrogen chloride in anhydrous ethanol. The mixture was concentrated to one-tenth its original volume and 50 ml of diethyl ether was added. The mixture was poured into ice water, the layers were separated, and the ethereal layer was washed successively with saturated aqueous sodium bicarbonate and sodium chloride. The washed ether solution was dried over magnesium sulfate and distilled to give 436 mg (92% yield) of ethyl 2(β,β-dichlorovinyl)-3,3-dimethylcyclopropanecarboxylate, b.p. 75°–76°/0.25 mm. Gas chromatographic analysis indicated the cis:trans ratio to be about 2:8. The nmr spectrum of the trans isomer was distinguished by the absorption pattern: (β ppm: CCl$_4$) 5.56 (d, 1H), 4.05 (b.q., 2H), 2.12 (d.d., 1H), 1.47 (d, 1H), 1.50–1.10 (m, 9H); whereas specific absorption due to the cis isomer was observed at 6.22 (d) and 2.35–2.10 (m).

2 Using sodium t-butoxide in tetrahydrofuran

A solution of 547 mg (2 mmoles) of ethyl 4,6,6-trichloro-3,3-dimethyl-5-hexenoate an 2 ml of dry tetrahydrofuran was added dropwise to a suspension of 288 mg (3 mmoles) of sodium t-butoxide in 10 ml of dry tetrahydrofuran. The mixture was stirred at room temperature for 2 hours, then poured into ice water. The aqueous mixture was extracted with diethyl ether, and the ether extract was dried over magnesium sulfate. The dried extract was distilled to give 427 mg (90% yield) of ethyl 2-(β,β-dichlorovinyl)-3,3-dimethylcyclopropanecarboxylate, b.p. 78°–79°/0.35 mm. Gas chromatographic analysis indicated the cis:trans ratio to be about 1:9.

C. From ethyl 2(β,β,β-trichloroethyl)-3,3-dimethylcyclopropanecarboxylate (an Intermediate Z)

A solution of 2.72 g (0.01 mole) of ethyl 2-(β,β,β-trichloroethyl)-3,3-dimethylcyclopropanecarboxylate in 20 ml of absolute ethanol was added dropwise to a solution of 250 mg (0.011 mole) of sodium in 80 ml of absolute ethanol. The mixture was heated under reflux for 5 hours, then cooled with ice, and the cold mixture was neutralized with dry hydrogen chloride. The mixture was concentrated to one-tenth its original volume, then diluted with diethyl ether. The ether solution was washed successively with saturated aqueous sodium bicarbonate and water. The solution was dried over magnesium sulfate and distilled to give 1.94 g (82% yield) of ethyl 2(β,β-dichlorovinyl)-3,3-dimethylcyclopropanecarboxylate, b.p. 75°–76°/0.25 mm.

EXAMPLE XIV

Synthesis of Ethyl 2-(β,β-Dibromovinyl)-3,3-dimethylcyclopropanecarboxylate

A. Dehydrobromination of ethyl 4,6,6,6-tetrabromo-3,3-dimethylhexanoate

Two milliliters of an ethanolic solution containing 92 mg (4 mmoles) of sodium was added dropwise to a cold solution of 1.95 g (4 mmoles) of ethyl 4,6,6,6-tetrabromo-3,3-dimethylhexanoate in 10 ml of absolute ethanol. The cooled mixture was stirred for 2 hours, then poured into chilled 1N hydrochloric acid. The acidic mixture was extracted with diethyl ether, and the extract was washed successively with saturated aqueous sodium bicarbonate and sodium chloride. The washed extract was dried over magnesium sulfate and distilled to give 846 mg (52% yield) of ethyl 4,6,6-tribromo-3,3-dimethyl-5-hexenoate , b.p. 130°–133°/0.3 mm.

Analysis:

nmr δ ppm (CCl$_4$): 6.64 (d, 1H), 4.95 (d, 1H), 4.12 (q, 2H), 2.38 (b.d, 2H), 1.4–1.1 (m, 9H).

B. Cyclization of ethyl 4,6,6-tribromo-3,3-dimethyl-5-hexenoate (an Intermediate Y)

A solution of 407 mg (1 mmole) of ethyl 4,6,6-tribromo-3,3-dimethyl-5-hexenoate in 1.5 ml of absolute ethanol was added dropwise to a solution of 30 mg (1.3 mmoles) of sodium in 5 ml of absolute ethanol. The mixture was stirred for 3 hours at room temperature, then treated as described in Example XIII A to produce 270 mg (83% yield) of ethyl 2-(β, β-dibromovinyl)-3,3-dimethylcyclopropanecarboxylate, b.p. 95°–98°/0.3 mm.

Analysis:

nmr δ ppm (CCl$_4$): 6.70, 6.07 (d, 1H), 4.05 (q, 2H), 2.45–1.40 (m, 2H), 1.35–1.10 (m, 9H). ir (KBr, cm$^{-1}$): 1725, 1223, 1175, 855, 800, 762.

EXAMPLE XV

Synthesis of Other 2-Dihalovinylcyclopropanecarboxylates

A. Ethyl 2-(β,β-dichlorovinyl)-1,3,3-trimethylcyclopropanecarboxylate

1. From ethyl 4,6,6,6-tetrachloro-2,3,3-trimethylhexanoate

A solution of 1.3 g (4 mmoles) of ethyl 4,6,6,6-tetrachloro-2,3,3-trimethylhexanoate in 5 ml of anhydrous 1,2-dimethoxyethane was added dropwise to a suspension of 500 mg (10 mmoles) of 50% sodium hydride in 15 ml of the same solvent. The mixture was heated for 20 hours under reflux, then allowed to cool. The reaction mixture was neutralized by the addition of 1N hydrochloric acid and extracted with diethyl ether. The extract was washed with saturated aqueous sodium chloride, dried over magnesium sulfate and distilled to give 550 mg (55% yield) of ethyl 2-(β,β-dichlorovinyl)-1,3,3-trimethylcyclopropanecarboxylate, b.p. 71°–76°/0.08 mm.

The nmr spectrum of the product indicated that it consisted of 30% cis and 70% trans isomers. The trans isomer was distinguished by the absorption peaks (δ, ppm, CCl$_4$): 5.57 (d, 2H), 4.10 (b.q, 2H), 2.28 (d, 2H), 1.40–0.90 (m, 12H), while the cis isomer was distinguished by the absorption (δ, ppm. CCl$_4$): 6.26 (d, 2H) and 1.52 (d, 2H).

Analysis: nmr δ ppm (CCl$_4$): 6.26–5.57 (d, 1H), 4.10 (b.q, 2H), 2.28–1.52 (d, 1H), 1.40–0.90 (m, 12H).

2. From ethyl 4-bromo-6,6,6-trichloro-2,3,3-trimethylhexanoate

A solution of 368.5 mg (1 mmole) of 4-bromo-6,6,6-trichloro-2,3,3-trimethylhexanoate in 1ml of anhydrous tetrahydrofuran was added dropwise to a suspension of 224 mg (2 mmoles) of potassium t-butoxide in 10 ml of anhydrous tetrahydrofuran. The mixture was heated for 5 hours under reflux, poured into ice water, and the aqueous mixture was extracted with diethyl ether. The ether extract was dried over magnesium sulfate and distilled to give 55 mg (22% yield) of ethyl 2-(β,β-dichlorovinyl)-1,3,3-trimethylcyclopropanecarboxylate.

3. Via ethyl 6,6,6-trichloro-2,3,3-trimethyl-4-hexenoate (an Intermediate X)

A solution of 737 mg of ethyl 4-bromo-6,6,6-trichloro-2,3,3-trimethylhexanoate in 20 ml of anhydrous tetrahydrofuran was cooled to 0°. To the cold solution was added 163 mg of sodium ethoxide and the mixture was stirred for 5 hours. The cooled mixture was poured into cold 1N hydrochloric acid and extracted with diethyl ether. The ether extract was washed successively with water, saturated aqueous sodium bicarbonate and aqueous sodium chloride, then dried over magnesium sulfate. The dried ether extract was distilled to give 430 mg (75% yield) of ethyl 6,6,6-trichloro-2,3,3-trimethyl-4-hexenoate, b.p. 92°–95°/0.2 mm.

Analysis: nmr δ ppm (CCl$_4$): 6.15 (q, 2H), 4.07 (q, 2H), 2.70–2.10 m, 1H), 1.30–0.90 (m, 12H).

Two milliliters of an anhydrous 1,2-dimethoxyethane solution containing 547 mg of ethyl 6,6,6-trichloro-2,3,3-trimethyl-4-hexenoate was added dropwise to a suspension of 168 mg of 50% sodium hydride in 10 ml of anhydrous 1,2-dimethoxyethane. The mixture was heated under reflux for 12 hours, allowed to cool to room temperature, then neutralized by the addition of an anhydrous solution of hydrogen chloride in diethyl ether. The neutralized mixture was poured into ice water and extracted with diethyl ether. The extract was dried over magnesium sulfate and distilled to give 308 mg (65% yield) of ethyl 2-(β,β-dichlorovinyl)-1,3,3-trimethylcyclopropanecarboxylate, b.p. 75°–80°/0.2 mm.

4. Via ethyl 4,6,6-trichloro-2,3,3-trimethyl-5-hexenoate (an Intermediate Y)

A mixture of 288 mg of ethyl 6,6,6-trichloro-2,3,3-trimethyl-4-hexenoate (an Intermediate X) and 30 mg of phenol in 1 ml of xylene was refluxed for 10 hours under an argon atmosphere. Distillation gave 196 mg (68% yield) of ethyl 4,6,6-trichloro-2,3,3-trimethyl-5-hexenoate, b.p. 91°–93°/0.12 mm.

Analysis: nmr δ ppm (CCl$_4$): 5.95–5.94 (d, 1H), 4.77–4.62 (d, 1H), 4.03–4.02 (q, 2H), 2.80–2.35 (m, 1H), 1.35–0.90 (m, 12H).

A solution of 575 mg (2 mmoles) of ethyl 4,6,6-trichloro-2,3,3-trimethyl-5-hexenoate in 5 ml of anhydrous 1,2-dimethoxyethane was added dropwise to a dispersion of 120 mg (2.5 mmoles) of 50% sodium hydride in 10 ml of anhydrous 1,2-dimethoxyethane. The mixture was heated under reflux for 5 hours, then cooled. The cooled mixture was neutralized with 1 N hydrochloric acid and extracted with diethyl ether. The ether extract was washed successively with saturated aqueous sodium bicarbonate and sodium chloride. The washed extract was dried over magnesium sulfate, then distilled to give 360 mg (72% yield) of ethyl 2-(β,β-dichlorovinyl)-1,3,3-trimethylcyclopropanecarboxylate, b.p. 75°–78°/0.1 mm.

B. Ethyl 2-(β,β-dichlorovinyl)-3-methylcyclopropanecarboxylate

1. From ethyl 4,6,6,6-tetrachloro-3-methylhexanoate

A solution of 592 mg of ethyl 4,6,6,6-tetrachloro-3-methylhexanoate in 5 ml of absolute ethanol was added dropwise with stirring to a solution of 69 mg of sodium in 15 ml of absolute ethanol. After 5 hours the mixture was refluxed for 2 hours, then allowed to cool to room temperature, and neutralized by the addition of a solution of hydrogen chloride in anhydrous diethyl ether. The mixture was poured into ice water, extracted with diethyl ether, and the ether extract was dried over magnesium sulfate. The dried solution was distilled to give 292 mg (66% yield) of ethyl 2-(β,β-dichlorovinyl-3-methylcyclopropanecarboxylate, b.p. 70°–77°/0.5 mm.

Analysis:
ir (KBr, cm$^{-1}$): 3040, 1725, 1615, 1190, 1045, 922, 883, 861, 824, 645.

2. From ethyl 4-bromo-6,6,6-trichloro-3-methylhexanoate

A solution of 681 mg of ethyl 4-bromo-6,6,6-trichloro-3-methylhexanoate was treated as described immediately above to produce 276 mg (62% yield) of ethyl 2-(β,β-dichlorovinyl)-3-methylcyclopropanecarboxylate, b.p. 66°–72°/0.3 mm.

3. From ethyl 6,6,6-trichloro-3-methyl-4-hexenoate (an intermediate X)

One milliliter of a solution of 259.5 mg of ethyl 6,6,6-trichloro-3-methyl-4-hexenoate in anhydrous ethanol was added dropwise to a solution of 46 mg of sodium in 10 ml of the same solvent. The mixture was heated under reflux for 3 hours, allowed to cool, then neutralized by adding an ethereal solution of dry hydrogen chloride in ether. The neutralized mixture was poured into ice water and extracted with ether. The extract was dried over magnesium sulfate and distilled to give 156 mg (70% yield) of ethyl 2-(β,β-dichlorovinyl)-3-methylcyclopropanecarboxylate, b.p. 62°–66°/0.3 mm.

C. Ethyl 2-(β, β-dichlorovinyl)-3-phenylcyclopropanecarboxylate

In the manner of Example XV B.1, 716 mg of ethyl 4,6,6,6-tetrachloro-3-phenylhexanoate was reacted to obtain 274 mg (48% yield) of ethyl 2-(β,β-dichlorovinyl)-3-phenylcyclopropanecarboxylate, b.p. 105°–115°/0.1 mm. The nmr spectrum of the product indicated that it consisted of a mixture of isomers; the prominent nmr absorptions were as follows:

nmr δ ppm (CCl$_4$): 7.20 (m, 5 H), 6.10 (b.d, 0.5 H), 5.13 (d, 0.5 H), 4.17 (b.q, 2 H), 3.10–2.00 (m, 3 H), 1.32 (b.t, 3 H).

D. Benzyl 2-(β, β-dichlorovinyl)-3,3-dimethylcyclopropanecarboxylate

A solution of 335.7 mg of benzyl 4,6,6,6-tetrachloro-3,3-dimethylhexanoate in 2 ml of anhydrous tetrahydrofuran was added dropwise to a suspension of 192 mg of sodium t-butoxide in 8 ml of anhydrous tetrahydrofuran at 0°. The mixture was stirred for 2 hours at 0°, then for 0.5 hour at room temperature. The mixture was neutralized by adding a solution of dry hydrogen chloride in ether. The neutral solution was washed with water, then dried over magnesium sulfate. The dried solution was distilled to give 210 mg (77% yield) of benzyl 2-(β,β-dichlorovinyl)-3,3-dimethylcyclopropanecarboxylate, b.p. 114°–118°/0.13 mm.

Analysis: Calc'd for $C_{15}H_{16}Cl_2O_2$: C, 60.22; H, 5.39; Cl, 23.70. Found: C, 60.12; H, 5.39; Cl, 23.90.

nmr δ ppm (CCl$_4$): 7.22 (b.s., 5 H), 6.18 (d, 0.5 H), 5.50 (d, 0.5 H), 5.01 (s, 2 H), 2.4–1.5 (m, 2 H), 1.42–1.05 (m, 6 H).

E. The following compounds can be prepared by similar methods:

1. ethyl 2-(β,β-dichlorovinyl)cyclopropanecarboxylate
2. ethyl 3-benzyl-2-(β,β-dichlorovinyl)cyclopropanecarboxylate
3. ethyl 2-(β,β-dichlorovinyl)-3-isopropyl-3-methylcyclopropanecarboxylate
4. ethyl 1-benzoyl-3-(2-butenyl)-2-(β,β-dichlorovinyl)-3-ethylcyclopropanecarboxylate
5. methyl 2-(β,β-dichlorovinyl)-3-methyl-3-phenylcyclopropanecarboxylate 6. ethyl 2-(β,β-dichlorovinyl)spiro[2.5]octane-1-carboxylate 7. methyl 3-allyl-3-carbomethoxy-2-(β,β-dichlorovinyl)cyclopropanecarboxylate 8. methyl 3-carbomethoxy-2-(β,β-dichlorovinyl)-3-cyanocyclopropanecarboxylate 9. ethyl 3-acetyl-1-benzyl-2-(β,β-dichlorovinyl)-1-cyclohexyl-3-ethylcyclopropanecarboxylate 10. methyl 3-benzoyl-2-(β,β-dibromovinyl)-3-phenylcyclopropanecarboxylate 11. ethyl 3-acetyl-2-(β,β-dibromovinyl)-3-(N,N-dimethylcarboxamido)cyclopropanecarboxylate 12. ethyl 3-cyano-2-(β,β-difluorovinyl)-3-methylcyclopropanecarboxylate 13. ethyl 2-(β,β-dichlorovinyl)-1-ethyl-3,3-dimethylcyclopropanecarboxylate 14. propyl 2-(β-bromo-β-chlorovinyl)-1,3-dimethylcyclopropanecarboxylate 15. methyl 2-(β,β-difluorovinyl)-3,3-dimethyl-1-phenylcyclopropanecarboxylate 16. ethyl 1-vinyl-2-(β,β-dichlorovinyl)-3-cyclohexyl-3-ethylcyclopropanecarboxylate 17. methyl 1-carboisopropoxy-2-(β,β-dibromovinyl)-3,3-dimethylcyclopropanecarboxylate 18. ethyl 1-acetyl-2-(β,β-dichlorovinyl)-3,3-dimethylcyclopropanecarboxylate 19. methyl 1-butyryl-2-(β,β-dichlorovinyl)-3-cyanocyclopropanecarboxylate 20. ethyl 2-(β,β-dibromovinyl)-1-(N,N-dimethylcarboxamido)-3-methylcyclopropanecarboxylate 21. methyl 1-cyano-2-(β,β-difluorovinyl)-3-phenylcyclopropanecarboxylate 22. ethyl 1-ethynyl-2-(β,β-dichlorovinyl)-3,3-dimethylcyclopropanecarboxylate

EXAMPLE XVI

Synthesis of Cyclopropanecarboxylates Containing Other β-Substituents

A. Preparation of ethyl 1,3,3-trimethyl-2-vinylcyclopropanecarboxylate

1. A mixture of 920 mg (5 mmoles) of ethyl 2,3,3-trimethyl-4-hexenoate, 10 ml of carbon tetrachloride, 107 mg (6 mmoles) of N-bromosuccinimide, and 50 mg of benzoyl peroxide was heated under reflux for about two hours. The insoluble succinimide was removed by filtration. The filtrate was washed successively with saturated aqueous sodium bicarbonate solution and water, then dried over magnesium sulfate. The dried solution was distilled to give 1.14 g (86% yield) of ethyl 6-bromo-2,3,3-trimethyl-4-hexenoate, b.p. 80°–81°/0.8 mm.

Analysis:
nmr δ ppm (CCl$_4$): 5.84–5.37 (m, 2 H), 4.01 (q, 2 H), 3.85 (d, 2 H), 2.24 (q, 1 H), 1.22 (t, 3 H), 1.13–0.97 (m, 9 H).

2. A solution of 526 mg (2 mmoles) of ethyl 6-bromo-2,3,3-trimethyl-4-hexenoate in 2 ml of anhydrous tetrahydrofuran was added dropwise to a suspension of 224 mg (2 mmoles) of potassium t-butoxide in 10 ml of tetrahydrofuran. The mixture was heated under reflux for two hours and then allowed to cool to room temperature. An additional 116 mg (1 mmole) of potassium t-butoxide was added, and the mixture again heated under reflux for two hours. The reaction mixture was poured into ice water, and the aqueous mixture extracted with diethyl ether. The ether extract was dried over magnesium sulfate and distilled to give 200 mg (55% yield) of ethyl 1,3,3-trimethyl-2-vinylcyclopropanecarboxylate, b.p. 92°–95°/1.5 mm.

Analysis:
nmr δ ppm (CCl$_4$): 6.40–4.80 (m, 3 H), 4.03 (b.q. 2 H), 2.08 (b.d, 1 H), 1.40–1.00 (m, 12 H).

B. Preparation of ethyl 3,3-dimethyl-2-vinylcyclopropanecarboxylate 1. By the method of Example XVI-A1 there was prepared ethyl 6-bromo-3,3-dimethyl-4-hexenoate, b.p. 85°–0.5 mm.

Analysis:
ir (cm$^{-1}$): 1730, 1365, 1215, 1033, 970, 710, 590.

2. By the method of Example XVI-A2 ethyl 6-bromo-3,3-dimethyl-4-hexenoate was converted to ethyl 3,3-dimethyl-2-vinylcyclopropanecarboxylate, b.p. 68°–75°/25 mm.

Analysis: ir (cm$^{-1}$): 1728, 1630, 1187, 1148, 1097, 1030, 990, 902.

We claim:
1. A process for preparing the compound

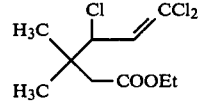

which comprises dehydrohalogenating ethyl 4,6,6,6-tetrachloro-3,3-dimethylhexanoate in dimethylformamide with sodium ethoxide at a temperature between about 50° and 150° C. to eliminate one mole of HCl and produce said compound.

* * * * *